(12) United States Patent
Neumeyer et al.

(10) Patent No.: US 9,517,279 B2
(45) Date of Patent: Dec. 13, 2016

(54) 2-ALKOXY-11-HYDROXYAPORPHINE DERIVATIVES AND USES THEREOF

(75) Inventors: John L. Neumeyer, Wayland, MA (US); Yu-Gui Si, Shanghai (CN); Anna W. Sromek, Belmont, MA (US)

(73) Assignee: The McLean Hospital Corporation, Belmont, MA (US)

( * ) Notice: Subject to any disclaimer, the term of this patent is extended or adjusted under 35 U.S.C. 154(b) by 352 days.

(21) Appl. No.: 13/640,426

(22) PCT Filed: Apr. 14, 2011

(86) PCT No.: PCT/US2011/032522
§ 371 (c)(1),
(2), (4) Date: Mar. 22, 2013

(87) PCT Pub. No.: WO2011/130530
PCT Pub. Date: Oct. 20, 2011

(65) Prior Publication Data
US 2013/0209362 A1    Aug. 15, 2013

Related U.S. Application Data

(60) Provisional application No. 61/324,081, filed on Apr. 14, 2010.

(51) Int. Cl.
| | | |
|---|---|---|
| A61K 51/00 | (2006.01) | |
| A61M 36/14 | (2006.01) | |
| A61K 51/04 | (2006.01) | |
| C07D 221/18 | (2006.01) | |

(52) U.S. Cl.
CPC ......... *A61K 51/0455* (2013.01); *C07D 221/18* (2013.01)

(58) Field of Classification Search
CPC ................ A61K 51/0455; C07D 221/18
USPC ......................................... 424/1.89
See application file for complete search history.

(56) References Cited

U.S. PATENT DOCUMENTS

| | | |
|---|---|---|
| 3,717,643 A | 2/1973 | Archer |
| 4,353,912 A | 10/1982 | Neumeyer |
| 4,543,256 A | 9/1985 | Neumeyer |
| 4,687,773 A | 8/1987 | Neumeyer et al. |
| 5,446,147 A | 8/1995 | Kung et al. |
| 7,648,995 B2 | 1/2010 | Neumeyer et al. |
| 8,063,060 B2 | 11/2011 | Neumeyer et al. |
| 2011/0034446 A1 | 2/2011 | Neumeyer et al. |

FOREIGN PATENT DOCUMENTS

WO    WO-2009/009083 A1    1/2009

OTHER PUBLICATIONS

Si et al. Bioorg. Med. Chem Lett. 2008, 3971-3973.*
Booij et al. Eur. J. Nucl. Med. 1999, 171-182.*
Finnema et al. Nucl. Med. Biol. 2005, 353-360.*
Lasne et al. Top. Curr. Chem. 2002, 201-258.*
Patani et al. Chem. Rev. 1996, 3147-3176.*
Chi et al. J. Org. Chem. 1987, 658-664.*
Zhang et al. Curr. Top. Med. Chem. 2007, 1817-1828.*
Steiger et al. J. Labell. Cmpd. Radiopharm. 2009, 158-165.*
Gao et al. J. Med. Chem. 1990, 1800-1805.*
International Preliminary Report on Patentability for International Application No. PCT/US2011/032522, dated Oct. 26, 2012.
Toyama et al., "Dopamine D2 receptor Spect imaging: basic in vivo characteristics and clinical applications of 123I-IBZM in humans," *Ann. Nucl. Med.* 7:29-38, 1993.
International Search Report and Written Opinion for International Application No. PCT/US11/32522, dated Jun. 24, 2011.
Finnema et al., "18F-MCL-524, an 18F-Labeled Dopamine D2 and D3 Receptor Agonist Sensitive to Dopamine: A Preliminary PET Study," *J Nucl Med.* 55(7):1164-70 (2014).
Böhm et al., "Fluorine in medicinal chemistry," *Chembiochem.* 5(5):637-43 (2004).

\* cited by examiner

*Primary Examiner* — Michael G Hartley
*Assistant Examiner* — Sean R Donohue
(74) *Attorney, Agent, or Firm* — Clark & Elbing LLP

(57) ABSTRACT

The invention features 2-alkoxy-11-hydroxyaporphine derivatives that selectively bind $D_2^{high}$ receptors. The compounds are useful for imaging $D_2^{high}$ receptors and for the treatment of diseases, such as Parkinson's disease, sexual dysfunction, and depressive disorders.

18 Claims, No Drawings

2-ALKOXY-11-HYDROXYAPORPHINE DERIVATIVES AND USES THEREOF

CROSS-REFERENCE TO RELATED APPLICATIONS

This application is the U.S. National Stage filing under 35 U.S.C. §371 of International Application No. PCT/US2011/032522, filed Apr. 14, 2011, which claims the benefit of U.S. Provisional Pat. Application No. 61/324,081, filed Apr. 14, 2010.

BACKGROUND OF THE INVENTION

The invention relates to the treatment of Parkinson's disease, sexual dysfunction, stroke, and depressive disorders, and to the diagnosis of conditions associated with abnormal D2 receptor function.

Dopamine is unarguably one of the most important neurotransmitters in the brain. Disturbances in the dopaminergic system, and especially irregularities in dopamine D2 receptor function, have been implicated in many different neurological and psychiatric disorders, including Parkinson's disease, Huntington's chorea, schizophrenia, attention deficit-hyperactivity disorder, Tourette's syndrome, restless leg syndrome, and addiction (see Bozzi, et al., TRENDS in Neurosciences 29:167 (2006); and Marsden, C.A. British J. Pharm. 147:S136 (2006)). Early diagnosis of these disorders is desirable, as early treatment of the disease would allow for a better outcome for the patient, by slowing the progression of the disease and lessening the severity of the symptoms or future episodes. Physical symptoms tend to manifest themselves much later, after significant changes occur in the brain. Thus, identification of subtle changes in the brain early in the course of the disease, before a clinical diagnosis from physical symptoms can be made, would offer the best opportunity for early treatment.

Parkinson's disease is a progressive neurodegenerative disorder of the basal ganglia of the brain, which most often becomes apparent after the age of 55. It is a prevalent and prototypic hypokinetic disorder, with akinesia, bradykinesia, rigidity and tremor as the most prominent features. The neurological and psychiatric symptoms, including depression and psychosis, with late dementia, usually worsen with time. The neuropathology of Parkinson's disease reveals a striking and selective loss of the dopaminergic neurons of the nigrostriatal pathway of the brain.

As Parkinson's disease is associated with a loss of the neurotransmitter dopamine, it is commonly treated with drugs which replace or mimic the actions of dopamine. Since dopamine itself cannot pass the blood-brain diffusion barrier, the most commonly used therapy is levodopa (L-DOPA), the immediate precursor of dopamine which is readily decarboxylated by remaining dopaminergic neurons and other amine-producing neurons. A complication of long-term treatment with L-DOPA is the development of rapid fluctuations in clinical state such that the patient changes, often abruptly, between mobility and immobility; this phenomenon is known as the 'on-off' effect.

An alternative approach to treatment with L-DOPA is the use of drugs (dopamine agonists and partial-agonists) that mimic the actions of dopamine. Treatment with dopamine receptor agonists has some advantages over treatment with L-DOPA. Unlike L-DOPA, dopamine agonists are effective in patients with advanced stages of Parkinson's disease because their action at postsynaptic receptors is unaffected by the lack of dopamine producing nerve cells that decarboxylate L-DOPA to produce dopamine locally, whereas the denervated dopamine receptors are supersensitive to agonists. Furthermore, there is an increasing interest in the potential of dopamine receptor agonists to provide a neuroprotective effect. Theoretically, such a protective effect might result from (i) a decreased need for the use of L-DOPA, a substance that may cause oxidative stress and perhaps even contribute to further damage of dopamine neurons, (ii) stimulation of dopamine autoreceptors resulting in decreased dopamine synthesis, release, and turnover, resulting in reduced metabolism of dopamine to reactive oxygen species, and (iii) by direct anti-oxidant effects.

R(−)-Apomorphine is a directly acting dopamine agonist at both $D_1$ and $D_2$ receptors, and dopamine autoreceptors, without opiate-like or addictive properties. Apomorphine therapy has led to sustained improvements in Parkinson's disease patients with refractory motor oscillations (on-off phenomena). However, it is difficult to administer owing to its poor bioavailability and extensive first-pass metabolism to inactive metabolites. Therefore, apomorphine is usually administered either by intermittent subcutaneous injection or continuous subcutaneous infusion. Following a single dose, apomorphine has an onset of action of 5-15 minutes, and its effects last for 40-60 minutes.

Direct dopamine agonists, including R(−)-apomorphine, are also effective in the treatment of a number of forms of sexual dysfunction, primarily, but not limited to erectile dysfunction. See Martinez et al., J. Urology 170:2352 (2003).

There are two general classes of dopamine receptors in the brain, type D1, which interacts with the $G_s$ complex to activate adenylyl cyclase, and type D2, which interacts with $G_i$ to inhibit cAMP production. Among these two classes exist at least five subtypes of dopamine receptors, $D_1$, $D_2$, $D_3$, $D_4$, and $D_5$. The $D_1$ and $D_5$ receptors have a D1-like pharmacology, whereas the $D_2$, $D_3$, and $D_4$ receptors have a D2-like pharmacological profile. The dopamine receptors are part of the general family of G protein-linked receptors. A receptor which is linked to a G protein (of which there are many types) can exist in two states. These two states are referred to as the high affinity state and low affinity state. For example, in the case of the dopamine receptor, dopamine has a dissociation constant of 1.5 nM for the high-affinity state, or $D_2^{High}$, and approximately 200-2000 nM for the low-affinity state, or $D_{2Low}$. Depending on local conditions in vitro or in vivo, the two states can quickly convert into each other. Because the high-affinity state is considered the functional state (George et al., Endocrinology 117: 690, 1985), the process of "desensitization" occurs whenever the high-affinity state converts into the low-affinity state.

Noninvasive imaging of molecular and biological processes in living subjects with positron emission tomography (PET) and single photon emission computed tomography (SPECT) are invaluable tools for the investigation of human neurochemistry and neuropharmacology in vivo (see, for example, Ametamey et al., Chem. Rev. 108:1501 (2008)). Extensive research efforts have been directed toward the development of PET and SPECT radioligands suitable for probing the dopaminergic system (see Abi-Dargham et al., J. Nucl. Med. 37:1129 (1996); Seibyl et al., J. Nucl. Med. 39:1500 (1998); Neumeyer et al., J. Med. Chem. 34:3144 (1991); Innis et al., Proc. Natl. Acad. Sci. USA. 90:11965 (1993); and Airaksinen, et al., Bioorg. Med. Chem. 16:6467 (2008).

Previous studies suggest that in certain neurological disorders, such as schizophrenia and other DA-dependent neurological disorders, more $D_2$ receptors exist in the $D_2^{high}$ state (see Seeman, P. Clin. Schizophrenia and Related Psychoses 351-355 (2008); Seeman et al., Proc. Natl. Acad. Sci. 102:3513 (2005); Seeman, P. Synapse 63:186 (2009) and Seeman, P. Synapse 62:314 (2008)), and that $D_2^{high}$ is the primary and common target for the antiparkinson action of dopamine agonists (see Seeman, P. Synapse 61:1013 (2007); Seeman et al., Synapse 58:122 (2005).

New compounds that discriminate between high affinity ($D_2^{high}$) and low affinity ($D_{2low}$) states of the $D_2$ receptor are needed for the treatment and diagnosis of diseases, such as Parkinson's disease and schizophrenia.

SUMMARY OF THE INVENTION

The invention is based on the discovery of R(−)-2-alkoxy-11-hydroxyaporphine derivatives that selectively bind $D_2^{high}$ receptors. The compounds are useful for imaging $D_2^{high}$ receptors and for the treatment of diseases, such as Parkinson's disease, sexual dysfunction, stroke, and depressive disorders.

In a first aspect, the invention features a compound of formula I or a pharmaceutically acceptable salt thereof.

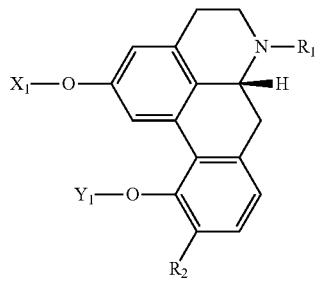

(I)

In formula I, $X_1$ is a $C_{1-3}$ fluoroalkyl or a $C_{1-3}$ iodoalkyl; $R_1$ is H, $C_{1-4}$ alkyl, $C_{2-4}$ alkenyl, or $C_{2-4}$ alkynyl; $R_2$ is H or $OY_2$; each of $Y_1$ and $Y_2$ is, independently, selected from H, C(O)—$R_3$, C(O)—O—$R_3$, C(O)—$NR_3R_4$, P(O)(OH)—O—$R_3$, C(S)—$R_3$, C(S)—O—$R_3$, C(S)—$NR_3R_4$, and fatty acid acyl, or $Y_1$ and $Y_2$ combine with the oxygen atoms to which they are bound to form a cyclic acetal or cyclic ketal; and each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom. Desirably, $R_1$ is H, $CH_3$, $CH_2CH_3$, $CH_2CH_2CH_3$, $CH_2CH_2$=$CH_2$, or cyclopropylmethyl.

Compounds of formula I include those described by formula II or III and pharmaceutically acceptable salts thereof.

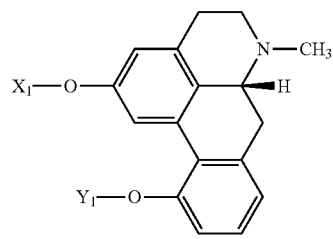

(IIa)

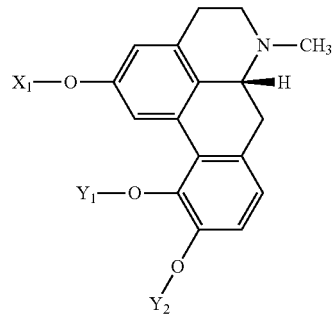

(IIIa)

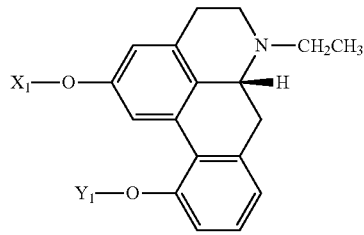

(IIb)

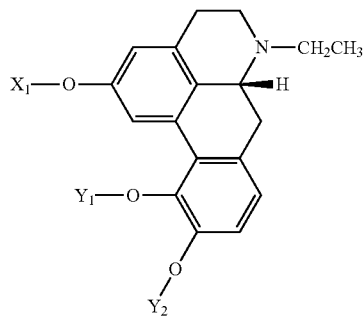

(IIIb)

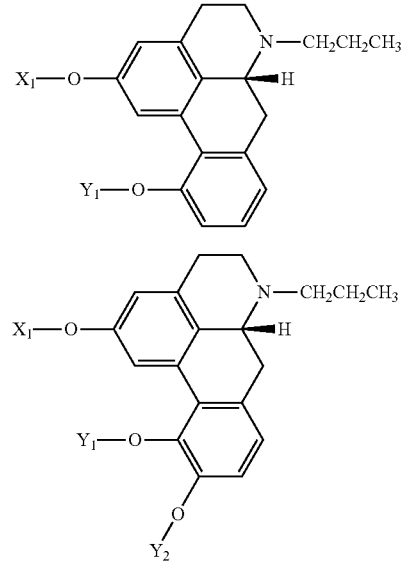

(IIc)

(IIIc)

In formulas II(a-c) and III(a-c), $X_1$, $Y_1$, and $Y_2$ are as defined above in formula I.

In certain embodiments of compounds of formula I, $R_1$ is $CH_3$, $CH_2CH_3$, or $CH_2CH_2CH_3$; and $X_1$ is fluoromethyl, difluoromethyl, trifluoromethyl, 2-fluoroethyl, 1-fluoroethyl, 1,2-difluoroethyl, 2,2-difluoroethyl, 2,2,2,-trifluoroethyl, 1,2-difluoroethylene, 2,2-difluoroethylene, pentafluoroethyl, 3-fluoro-n-propyl, 3,3-difluoro-n-propyl, 3,3,3- trifluoro-n-propyl, 3,3,3,2,2-pentafluoro-n-propyl, heptafluoro-n-propyl, 3,3,3-trifluoro-1-propene, 3,3,3-trifluoro-1-propyne, iodomethyl, iodoethyl, or iodopropyl.

In particular embodiments of compounds of any of formulas I-III(c), $X_1$ is a $C_{1-3}$ fluoroalkyl that includes a radioactive fluorine atom.

Compounds of formula I include those described by formulas IV and a pharmaceutically acceptable salts thereof.

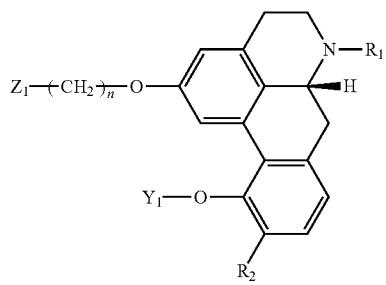

(IV)

In formula IV, $Z_1$ is a radioactive or nonradioactive fluorine atom or iodine atom; n is 1, 2, or 3; $R_1$ is H, $C_{1-4}$ alkyl, $C_{2-4}$ alkenyl, or $C_{2-4}$ alkynyl; $R_2$ is H or $OY_2$; each of $Y_1$ and $Y_2$ is, independently selected from H, C(O)—$R_3$, C(O)—O—$R_3$, C(O)—$NR_3R_4$, P(O)(OH)—O—$R_3$, C(S)—$R_3$, C(S)—O—$R_3$, C(S)—$NR_3R_4$, and fatty acid acyl, or $Y_1$ and $Y_2$ combine with the oxygen atoms to which they are bound to form a cyclic acetal or cyclic ketal; and each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom. Desirably, $R_1$ is H, $CH_3$, $CH_2CH_3$, $CH_2CH_2CH_3$, $CH_2CH_2$=$CH_2$, or cyclopropylmethyl. In particular embodiments, $Z_1$ is a radioactive fluorine atom.

Compounds of formula I can include, without limitation, the following compounds optionally bearing a radioactive fluorine atom and pharmaceutically acceptable salts thereof:
(i) R(−)-2-(trifluoromethoxy)-11-hydroxy-N-methyl-noraporphine, R(−)-2-(fluoromethoxy)-11-hydroxy-N-methyl-noraporphine, R(−)-2-(2-fluoroethoxy)-11-hydroxy-N-methyl-noraporphine, R(−)-2-(3-fluoro-n-propanoxy)-11-hydroxy-N-methyl-noraporphine, R(−)-2-(trifluoromethoxy)-11-hydroxy-N-ethyl-noraporphine, R(−)-2-(fluoromethoxy)-11-hydroxy-N-ethyl-noraporphine, R(−)-2-(2-fluoroethoxy)-11-hydroxy-N-ethyl-noraporphine, R(−)-2-(3-fluoro-n-propanoxy)-11-hydroxy-N-ethyl-noraporphine, R(−)-2-(trifluoromethoxy)-11-hydroxy-N-propyl-noraporphine, R(−)-2-(fluoromethoxy)-11-hydroxy-N-propyl-noraporphine, R(−)-2-(2-fluoroethoxy)-11-hydroxy-N-propyl-noraporphine, R(−)-2-(3-fluoro-n-propanoxy)-11-hydroxy-N-propyl-noraporphine, and 11-O-acyl esters thereof (e.g., 11-O-acetyl, 11-O-propionyl, 11-O-isobutyryl, 11-O-butyryl, 11-O-isovaleryl, 11-O-valeryl, and fatty acid esters); and (ii) R(−)-2-(trifluoromethoxy)-10-hydroxy-11-hydroxy-N-methyl-noraporphine, R(−)-2-(fluoromethoxy)-10-hydroxy-11-hydroxy-N-methyl-noraporphine, R(−)-2-(2-fluoroethoxy)-10-hydroxy-11-hydroxy-N-methyl-noraporphine, R(−)-2-(3-fluoro-n-propanoxy)-10-hydroxy-11-hydroxy-N-methyl-noraporphine, R(−)-2-(trifluoromethoxy)-10-hydroxy-11-hydroxy-N-ethyl-noraporphine, R(−)-2-(fluoromethoxy)-10-hydroxy-11-hydroxy-N-ethyl-noraporphine, R(−)-2-(2-fluoroethoxy)-10-hydroxy-11-hydroxy-N-ethyl-noraporphine, R(−)-2-(3-fluoro-n-propanoxy)-10-hydroxy-11-hydroxy-N-ethyl-noraporphine, R(−)-2-(trifluoromethoxy)-10-hydroxy-11-hydroxy-N-propyl-noraporphine, R(−)-2-(fluoromethoxy)-10-hydroxy-11-hydroxy-N-propyl-noraporphine, R(−)-2-(2-fluoroethoxy)-10-hydroxy-11-hydroxy-N-propyl-noraporphine, R(−)-2-(3-fluoro-n-propanoxy)-10-hydroxy-11-hydroxy-N-propyl-noraporphine, 10-O-acyl-11-O-acyl diesters thereof (e.g., 10,11-O-diacetyl, 10,11-O-dipropionyl, 10,11-O-diisobutyryl, 10,11-O-dibutyryl, 10,11-O-diisovaleryl, and 10,11-O-divaleryl esters), and 10,11 cyclic acetals and ketals thereof.

The invention further features a compound of formula V or a pharmaceutically acceptable salt thereof.

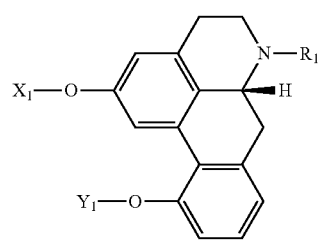

(V)

In formula V, $X_1$ is a $C_{1-3}$ alkyl, $C_{1-3}$ alkenyl, or $C_{1-3}$ alkynyl; $R_1$ is $CH_3$ or $CH_2CH_3$; $Y_1$ is selected from H, C(O)—$R_3$, C(O)—O—$R_3$, C(O)—$NR_3R_4$, P(O)(OH)—O—$R_3$, C(S)—$R_3$, C(S)—O—$R_3$, C(S)—$NR_3R_4$, and fatty acid acyl; and each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom.

In certain embodiments, the compound of formula V is selected from R(−)-2-(methoxy)-11-hydroxy-N-methyl-noraporphine, R(−)-2-(ethoxy)-11-hydroxy-N-methyl-noraporphine, R(−)-2-(n-propanoxy)-11-hydroxy-N-methyl-noraporphine, R(−)-2-(methoxy)-11-hydroxy-N-ethyl-noraporphine, R(−)-2-(ethoxy)-11-hydroxy-N-ethyl-noraporphine, R(−)-2-(n-propanoxy)-11-hydroxy-N-ethyl-noraporphine, esters thereof, and pharmaceutically acceptable salts thereof.

In certain embodiments of any of the above aspects, the compound of the invention can have an in vitro affinity of between 0.7 nM and 35 nM at $D_2^{high}$ receptors (e.g., between 0.5 nM and 50 nM, 0.7 nM and 30 nM, 0.7 nM and 20 nM, or 1.0 nM and 15 nM); and/or an in vitro affinity of between 200 nM and no observable affinity at $D_3$ receptors (e.g., between 400 nM and no observable affinity, between 800 nM and no observable affinity, or no observable affinity at $D_3$ receptors); and/or no observable affinity at $D_1^{high}$ receptors.

The invention further features compounds of formula VI or a pharmaceutically acceptable salt thereof.

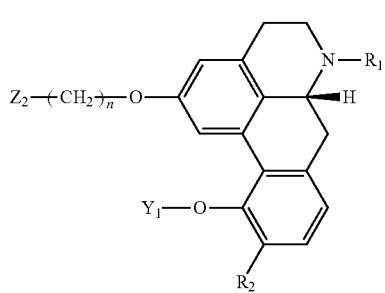

(VI)

In formula VI, $Z_2$ is OH or a leaving group capable of being displaced by a fluoride anion; n is 1, 2, or 3; $R_1$ is H, $C_{1-4}$ alkyl, $C_{2-4}$ alkenyl, or $C_{2-4}$ alkynyl; $R_2$ is H or $OY_2$; each of $Y_1$ and $Y_2$ is, independently selected from H, $C(O)$—$R_3$, $C(O)$—O—$R_3$, $C(O)$—$NR_3R_4$, $P(O)(OH)$—O—$R_3$, $C(S)$—$R_3$, $C(S)$—O—$R_3$, $C(S)$—$NR_3R_4$, and fatty acid acyl, or $Y_1$ and $Y_2$ combine with the oxygen atoms to which they are bound to form a cyclic acetal or cyclic ketal; and each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom. Desirably, $R_1$ is H, $CH_3$, $CH_2CH_3$, $CH_2CH_2CH_3$, $CH_2CH_2$=$CH_2$, or cyclopropylmethyl.

In particular embodiments of the compounds of formula VI, the $Z_2$ is leaving group selected from chloride, bromide, iodide, mesylate, tosylate and triflate.

Compounds of formula VI include those described by and of formulas VII or VIII and pharmaceutically acceptable salts thereof.

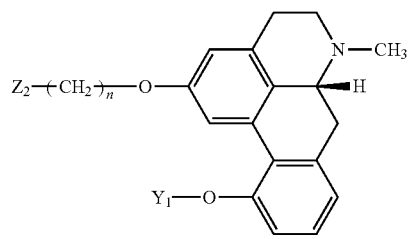

(VIIa)

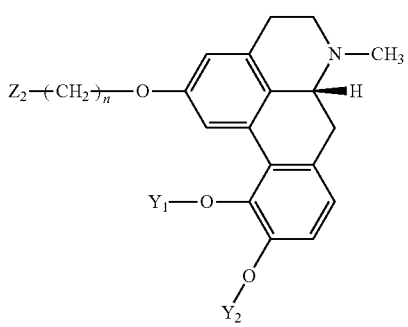

(VIIIa)

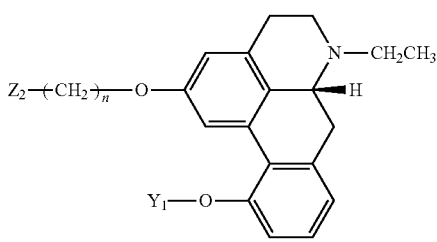

(VIIb)

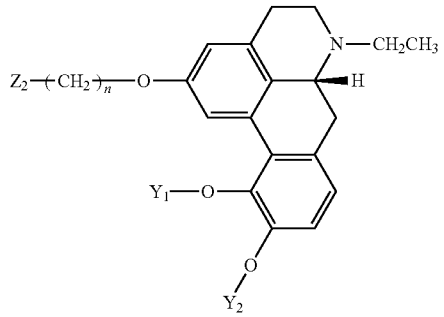

(VIIIb)

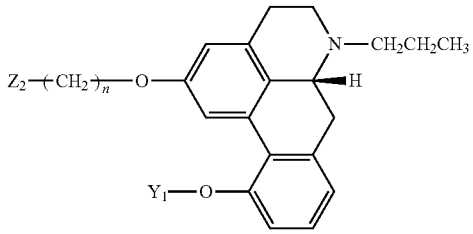

(VIIc)

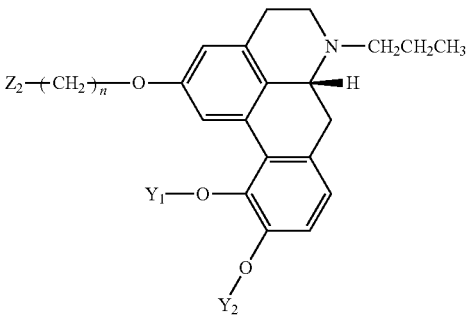

(VIIIc)

In formulas VII(a-c) and VIII(a-c), $Z_2$, $Y_1$, and $Y_2$ are as defined above in formula VI.

In a related aspect, the invention features a kit including (i) a compound of any of formulas VI-VIII(c); and (ii) instructions for radiolabeling the compound.

The invention further features a method of imaging $D_2^{high}$ receptors in a subject by (i) administering to the subject a radiolabeled compound of any of formulas I-IV, and (ii) following the specific binding of the radiolabeled compound to said $D_2^{high}$ receptors, monitoring the distribution of the radiolabeled compound in the subject.

In certain embodiments, the radiolabeled compound includes a radioactive fluorine atom and the distribution of the radiolabeled compound in the subject's brain is observed using PET.

In still other embodiments, the radiolabeled compound includes a radioactive iodine atom and the distribution of the radiolabeled compound in the subject's brain is observed using SPECT.

The imaging methods of the invention can further include diagnosing a dopamine-related disorder in the subject on the basis of the results of the imaging.

In certain embodiments, the imaging methods of the invention are repeated to monitor the progression of a dopamine-related disorder in the subject.

Dopamine-related disorders which can be diagnosed and monitored using the compound of the invention include psychoses, schizophrenia, Parkinson's disease, progressive supranuclear palsy, and dopamine supersensitivity.

The invention also features a pharmaceutical composition comprising a compound of the invention together with a pharmaceutically acceptable excipient.

The invention features a method for treating Parkinson's disease, sexual dysfunction, stroke, or depressive disorders in a subject, e.g., a human patient, by administering an effective amount of a compound of any of formulas I-V. These compounds are particularly useful for treating depressive disorders, such as major depression, dysthymia, bipolar disorder (manic depression), and post traumatic stress disorder.

The invention further features a method of aiding recovery of cognitive function following brain injury in a subject by administering to the subject an effective amount of a compound of any of formulas I-V.

The invention also features a method of aiding neurological recovery following brain injury in a subject by administering to the subject an effective amount of a compound of any of formulas I-V.

The compounds of the invention can be administered systemically, including, for example, by intravenous, intramuscular, or subcutaneous injection, orally, by inhalation, or by topical or transdermal application. Alternatively, the compounds can be centrally administered using, for example, by an intrathecal, intracerebroventricular, or intraparenchemal injection. Desirably, the compounds are administered orally.

The term "administration" or "administering" refers to a method of giving a dosage of a pharmaceutical composition to a patient, where the method is, e.g., oral, topical, transdermal, by inhalation, intravenous, intraperitoneal, intracerebroventricular, intrathecal, or intramuscular. The preferred method of administration can vary depending on various factors, e.g., the components of the pharmaceutical composition, site of administration, and severity of the symptoms being treated.

By "aiding cognitive function" is meant using the methods of the invention to improve memory, communication, attention, perception, recognition, planning, or related skills in a subject having impaired cognitive function as a result of a brain injury in comparison to a subject suffering a brain injury of the same severity and type but left untreated.

By "aiding neurological recovery" is meant using the methods of the invention to ameliorate neurological abnormalities, such as motor, sensory, cognitive, memory, visual, coordination, and gait deficits in a subject having such neurological deficits as a result of a brain injury in comparison to a subject suffering a brain injury of the same severity and type but left untreated.

The term "brain injury" is a general term used to refer to a condition that results in central nervous system damage, irrespective of its pathophysiological basis, and includes both traumatic and nontraumatic brain injury. Among the most frequent origins of a "brain injury" are stroke and traumatic brain injury (TBI). The term "traumatic brain injury" and "TBI" refer to traumatic injuries to the brain which occur when physical trauma causes brain damage. For example, TBI can result from a closed head injury or a penetrating head injury. The term "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

By "depressive disorder" is meant any psychological or psychiatric disorder associated with symptoms of depressed mood. Treatable depressive disorders may be characterized by an inhibition or reduction of dopaminergic function in the nucleus accumbens, e.g., major depression, dysthymia, bipolar disorder (manic depression), and post-traumatic stress disorder.

The term "dopamine-related disorder" as used herein refers to any disorder, disease or condition which is the result of modulation of, or causes a modulation in, the activity at a dopamine receptor, in particular the $D_2^{high}$ receptors. Dopamine-related disorders include, without limitation, Parkinson's disease, psychoses, schizophrenia, addiction, attention-deficit hyperactivity disorder (ADHD or ADD), depression, Huntington's disease and progressive supranuclear palsy.

As used herein, the term "imaging" refers to qualitative or quantitative determinations of the amount or density of $D_2^{high}$ receptors localized in the brain of a subject.

As used herein, "sexual dysfunction" refers to disorders of orgasm, response timing, ejaculation, nociception, congestive arousal and erection, vasculogenic impairment, or desire. In males, the form of sexual dysfunction is typically erectile dysfunction, the inability to achieve and sustain an erection sufficient for intercourse. Females also can have sexual dysfunctions of arousal and orgasm that increase with age and are associated with the presence of vascular risk factors and onset of menopause. Some of the vascular and muscular mechanisms that contribute to penile erection in the male are believed to involve similar vasculogenic factors in female genital responses. Female sexual dysfunction includes a failure to attain or maintain vaginal lubrication-swelling responses of sexual excitement until completion of the sexual activity.

As used herein, the term "subject" refers to any mammal, including, for example, a human.

As used herein, the term "stroke" refers to a clinical event involving thrombotic or embolic occlusion of a blood vessel supplying the brain, or a brain hemorrhage. Occlusion or hemorrhage can involve brain arteries or veins. Typically, stroke is manifest by the abrupt onset of a focal neurologic deficit. The term "ischemic stroke" refers to stroke characterized by localized tissue anemia due to obstruction of the inflow of arterial blood. Ischemic stroke is usually caused by atherothrombosis or embolism of a major cerebral artery, but may also be caused by coagulation disorders or nonatheromatous vascular disease. As used herein, "treating" stroke includes administration of a compound of the present invention, or a pharmaceutically acceptable salt thereof, for the purpose of (1) preventing stroke, (2) inhibiting stroke or the symptoms of stroke in a subject that is experiencing or displaying the pathology or symptomatology of stroke (i.e., arresting further development of the pathology and/or symptomatology), (3) ameliorating stroke or the symptoms of stroke in a subject that is experiencing or displaying the pathology or symptomatology of stroke (i.e., reversing the pathology and/or symptomatology), and/or (4) enhancing functional recovery following stroke or reducing hospitalization following stroke. Thus, the methods of the invention can be used for preventing, treating, eradicating, ameliorating or otherwise reducing the severity of stroke. The methods can be used to treat acute stroke (e.g., therapy beginning within 3 hours of a stroke event), as well as for stroke recovery (e.g., therapy beginning at least 8 hours following a stroke event).

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a subject either for therapeutic or prophylactic purposes.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-3}$ fluoroalkyl" is meant a branched or unbranched alkyl, alkene, or alkyne group of 1 to 3 carbons that is substituted with at least one fluorine atom.

By "$C_{1-3}$ iodoalkyl" is meant a branched or unbranched alkyl, alkene, or alkyne group of 1 to 3 carbons that is substituted with at least one iodine atom.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "$C_{1-12}$ alkyl" is meant a branched or unbranched hydrocarbon group having from 1 to 12 carbon atoms. A $C_{1-12}$ alkyl may be substituted or unsubstituted, may optionally include monocyclic or polycyclic rings, and includes the $C_{1-4}$ alkyls above.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-12}$ alkenyl" is meant a branched or unbranched hydrocarbon group containing one or more double bonds and having from 2 to 12 carbon atoms. A $C_{2-12}$ alkenyl may be substituted or unsubstituted, may optionally include monocyclic or polycyclic rings, and includes the $C_{2-4}$ alkenyls above.

By "$C_{2-4}$ alkynyl" is meant a branched or unbranched hydrocarbon group containing one or more triple bonds and having from 2 to 4 carbon atoms. A $C_{2-4}$ alkynyl may optionally include monocyclic, bicyclic, or tricyclic rings, in which each ring desirably has five or six members. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-12}$ alkynyl" is meant a branched or unbranched hydrocarbon group containing one or more triple bonds and having from 2 to 12 carbon atoms. A $C_{2-12}$ alkynyl may be substituted or unsubstituted, may optionally include monocyclic or polycyclic rings, and includes $C_{2-4}$ alkynyls above.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, mono substituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" is meant bromine, chlorine, iodine, or fluorine.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "fatty acid acyl" is meant a chemical moiety with the formula R—C(O)—, wherein R is a partially-saturated straight chain or branched hydrocarbon group having between 12 and 26 carbon atoms. Fatty acid acyls are derived from fatty acids including, without limitation, those occurring naturally in the brain. For example, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). The fatty acids can be substituted or unsubstituted. Exemplary substituents include hydroxyl, halide, methyl, ethyl, propyl, isopropyl, butyl, and pentyl groups. Desirably, the fatty acid acyl is 4, 7, 10, 13, 16, 19 docosahexanoyl.

Other features and advantages of the invention will be apparent from the following Detailed Description and the claims.

DETAILED DESCRIPTION

The invention features R(−)-2-alkoxy-11-hydroxyaporphine derivatives that selectively bind $D_2^{high}$ receptors. The compounds are useful for imaging $D_2^{high}$ receptors and for the treatment of diseases, such as Parkinson's disease, sexual dysfunction, stroke, and depressive disorders. The compounds are described by formula I (below) in which $X_1$, $R_1$, $R_2$, and $Y_1$ are as defined above.

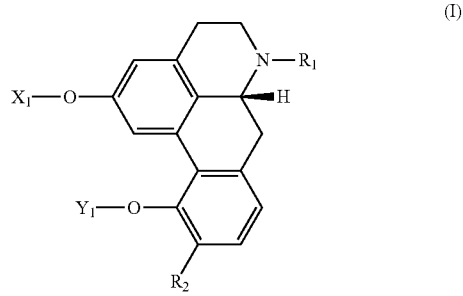

(I)

The invention also features starting materials for the synthesis of radiolabeled compounds (i.e., compounds of formula (VI)), useful for diagnosing and monitoring the progression of a dopamine-related disorder.

Synthesis

The synthesis of the thirteen target molecules (6,8a-g and 11a-d, g) and precursors 12b-d and 15 is shown in Scheme 1.

Scheme 1.
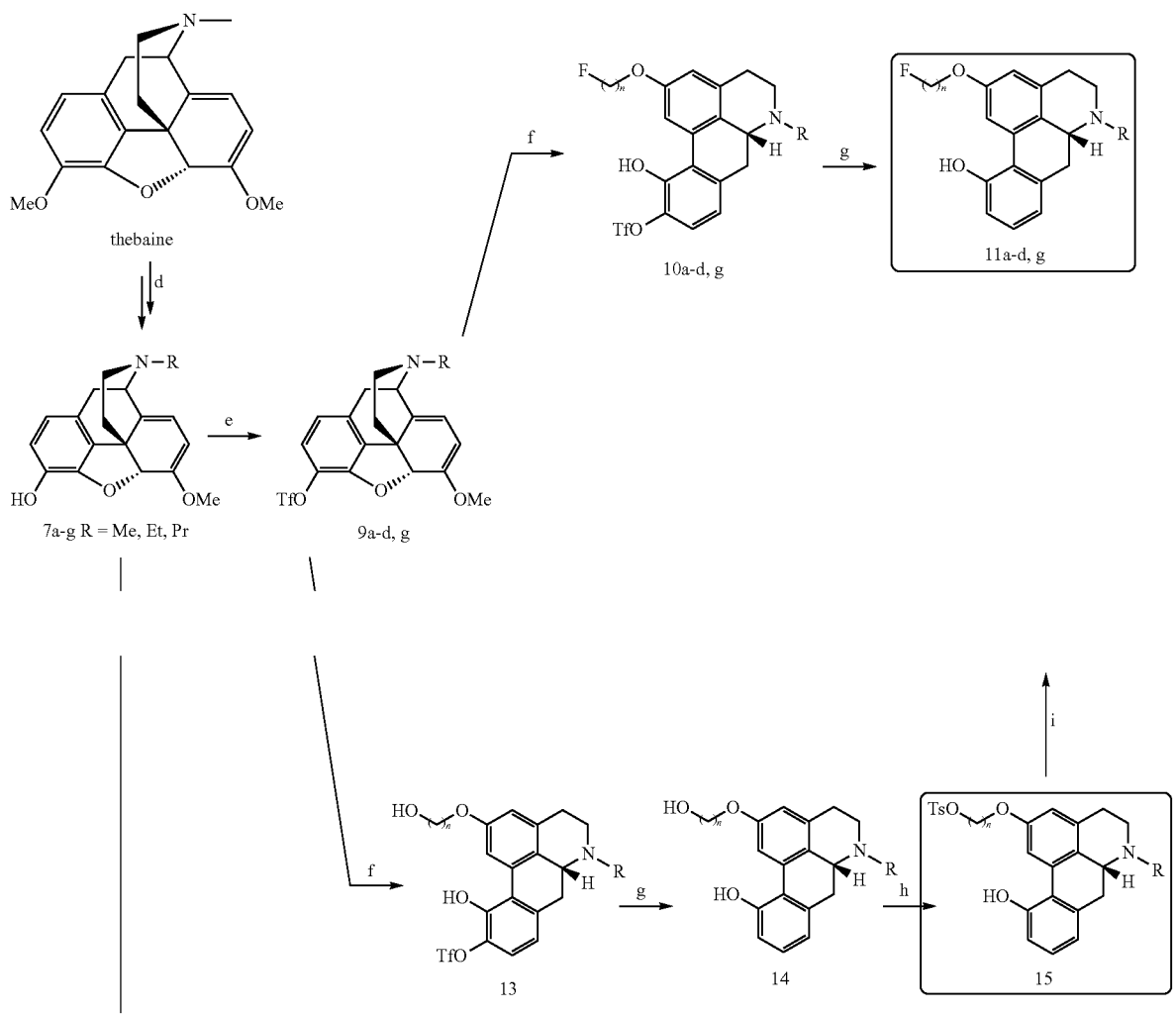

-continued

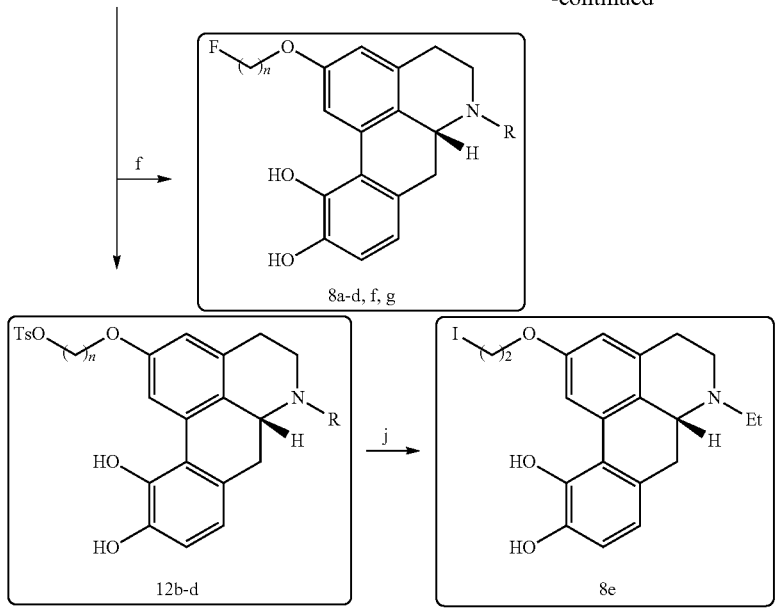

a) Si et al., J. Med. Chem. 51:983 (2008). b) 1-bromo-3-fluoropropane, NaHCO₃, EtOH/reflux;
c) MeSO₃H, 95° C.; d) Si, Y. G.; Neumeyer, J. L.; Synthesis, 24:3787 (2007). e) PhNTf₂, Et₃N, CH₂Cl₂; f) ROH, MeSO₃H, 95° C.; g) Pd/c, Mg, NH₄OAc, MeOH; h) TsCl, Et₃N, CH₂Cl₂; i) Kryptofix [2.2.2], KF, MeCN; j) NaI, acetone.

3-Deoxynormorphine 4 was prepared starting from morphine according to our published procedure in 4 steps (Csutoras et al., Bioorg. Med. Chem. Lett. 17:2687 (2004)). N-Alkylation of 4 with 1-bromo-3-fluoropropane led to the N-substituted-3-deoxynormorphine 5. Acid-catalyzed rearrangement of 5 with methanesulfonic acid at 90-100° C. yielded the target compound 11-hydroxy-N-(3-fluoropropyl)aporphine 6. Starting from thebaine, N-substituted nororipavines 7 were prepared in 4 steps using our previously reported procedure (Si et al., J. Med. Chem. 51:983 (2008)). Acid-catalyzed rearrangement of 7 with methanesulfonic acid at 90-95° C. (Sipos et al., Bioorg. Med. Chem. 16:4563 (2008)) in the presence of 2-fluoroethanol or 3-fluoropropanol yielded the corresponding fluorinated compounds 8. Rearrangement of the former in the presence of either ethylene glycol monotosylate or propanediol monotosylate afforded tosylated analogs 12. Tosylated noraporphine 12d was smoothly converted to iodinated noraporphine 8e under Finkelstein conditions. N-n-Propyl-3-O-[(trifluoromethyl)sulfonyl]nororipavines 9a-d were prepared in 5 steps from thebaine according the published procedure (Si, Y. G. and Neumeyer, J. L., Synthesis, 24:3787 (2007)). Oripavine-3-triflate 9g was prepared in one step from oripavine. Acid-catalyzed rearrangement of 9a-d, g with methanesulfonic acid at 90-100° C. yielded 10a-d, g followed by Pd/C catalyzed reduction with Mg metal in MeOH at room temperature in the presence of NH₄OAc (Si et al., J. Med. Chem. 51:983 (2008)) provided the target compounds 2-(fluoroalkoxy)-11-hydroxy-N-n-alkylnoraporphines 11a-d, g. In order to access 11-hydroxy-2-tosylalkoxyaporphines, nororipavine-3-triflates 9 underwent acid-catalyzed rearrangement in the presence of ethylene glycol to afford 11-hydroxy-2-hydroxyethoxy-10-trifluoromethylsulfonyloxy aporphines 13. Analogous reduction of the triflate group (Si et al., J. Med. Chem. 51:983 (2008)) followed by careful tosylation of the alcohol over the phenol (see U.S. Pat. No. 4,859,683) afforded tosylated aporphine derivative 15. The latter could be smoothly converted to fluorinated analog 11 by treatment with excess potassium fluoride in the presence of Kryptofix. Additional details are provided in the Examples.

Fatty acid acyl, ester, carbonate, phosphodiester, carbamate, cyclic ketal, and cyclic acetal derivatives of R(−)-11-hydroxyaporphines and R(−)-10,11-dihydroxyaporphines can be prepared using methods well known in the art for such modifications. For example, conditions for the modification of alcohols (i.e., to their corresponding fatty acid acyl, ester, carbonate, phosphodiester, carbamate, ketal, and acetal derivatives), as well as the conditions for the removal of such groups, can be found in T. W. Green and P. G. M. Wuts "Protective Groups in Organic Synthesis" (2$^{nd}$ ed., 1991, John Wiley & Sons) and P.J. Kocienski "Protecting Groups" (1994 Georg Thieme Verlag).

Activity at Dopamine Receptors

From the binding data shown in Table 1 (see Example 29), we observed that the cold compounds 6,8a-g and 11a-d, g showed good to high affinity at $D_2^{high}$ site, high selectivity of $D_2$ versus $D_1$, and low affinity or no affinity at all to the $D_3$ site. N-fluoropropyl aporphine 6 retained a similar binding affinity as N-propyl analog 3b to $D_2^{high}$ (6.9 and 4.9 nM, respectively). As shown in Table 1, a series of different N-n-propyl, ethyl, and methyl aporphines were synthesized and evaluated, with fluoropropanoxy and fluoroethoxy chains at position 2. The corresponding 10,11-dihydroxy and 11-hydroxy analogs, all aimed at achieving the best combination of binding affinity, selectivity, and lipophilicity, were also evaluated. It was reasoned that, although 10-deoxy aporphines tended to suffer a drop in $D_2$ binding affinities compared to the 10,11-dihydroxy analogs (see 3a, 3b, and 6 compared to 1, 2a, 2b, and 2c, Table 1), they were also far less prone to oxidation than the catechol-containing aporphines. We began by focusing on N-n-propyl aporphines, since these have been shown to consistently have higher $D_2$ binding affinities and selectivities over their N-ethyl and N-methyl counterparts (Gao et al., J. Med. Chem. 33:39 (1990)). Unfortunately, the 2-fluoropropanoxy analog 8a showed a drop in $D_2^{high}$ affinity compared to NPA 2a, 2-MeO-NPA 2b, and 2-F-NPA 2c (27 nM vs. 5.1 to 2.7 nM range). We were pleasantly surprised to find that by removing one carbon from the 2-substituent, 2-fluoroethoxy analog 8b restored $D_2^{high}$ affinity (3.7 nM) without compromising the remaining DA receptor affinity profile.

We next focused our attention on N-ethyl analogs. We were pleased to find that, in comparison to 8a, N-ethyl-2-fluoropropanoxy noraporphine 8c afforded about a 4-fold increase in $D_2^{high}$ affinity (6.1 vs. 28 nM) while simultaneously showing higher selectivity against $D_3$ (>10 μM vs. 430 nM). The 2-fluoroethoxy analog 8d afforded a more than 2-fold improvement in $D_2^{high}$ binding affinity (2.5 nM), while retaining a similar binding affinity profile among the other dopamine receptors tested. We were also pleased to find at this point that we could introduce iodine in place of fluorine and still retain a favorable binding profile, thus opening an avenue for the development of SPECT ligands. The iodoethoxy aporphine 8e, exhibited a slight drop in $D_2^{high}$ binding affinity compared to fluoro analog 8d; however, it retained high selectivity for $D_2^{high}$ over $D_1$, $D_3$, and $D_2^{low}$. Encouraged by these findings, next we investigated the N-methyl series. It was found that the 2-fluoropropanoxy aporphine 8f exhibited a $D_2^{high}$ affinity consistent with 8a (31 nM compared to 28 nM), although, unlike 8a or even 8c, it did not show any $D_3^{high}$ affinity. The 2-fluoroethoxy analog 8g afforded further improvement in $D_2^{high}$ binding over the N-propyl and N-ethyl analogs 8b and 8d (2.0 vs. 3.7 and 2.5 nM respectively), again with no detectable affinity to $D_3$. Finally, we investigated the series of 11-monohydroxy aporphines to determine the effect of the absence of the 10-hydroxy group on $D_2^{high}$ binding affinities. We synthesized the 10-deoxy analog 11g. Compound 11g was found to have a higher (1.2 nM) binding affinity to the $D_2^{high}$ receptor than 8g. Now with a lead compound in hand, we synthesized the tosyloxyethoxy derivative 15 as a precursor for the radiolabeled 11g. Next, we tested N-propyl-2-fluoroethoxy-11-monohydroxy aporphine 11b, the analogue of catecholaporphine 8b and found that the $D_2^{high}$ binding affinity was about the same. We were pleased to find that the N-ethyl 11-monohydroxy analogue 11d was found to have binding affinity on the order of 1 nM, and exhibiting an improved binding affinity than its 10,11-dihydroxy analogue 8d. Next, we tested N-ethyl-2-fluoropropanoxy-11-monohydroxy aporphine 11c, which also exhibited an overall improved binding affinity to $D_2^{high}$ as compared to its 10,11-dihydroxy analogue 8c. Unexpectedly, the last analogue, N-propyl-2-fluoropropanoxy-11-monohydroxy aporphine 11a, had the highest $D_2^{high}$ binding affinity of any of the aporphines studied. It was measured to have an average Ki value of 0.54 nM, which is at minimum an order of magnitude higher than its dihydroxy analogue 8a. Additional details are provided in Example 29.

In view of their selectivity for high affinity at $D_2^{high}$ site and high selectivity of $D_2$ versus $D_1$, the compounds of the invention can be useful for the treatment of neurological conditions characterized by dysfunction in $D_2^{high}$ activity and useful as radiotracers for the imaging of the DA $D_2$ high-affinity state using positron emission tomography or single proton emission computed tomography.

Imaging

Fluorine-18 ($^{18}F$) is the most attractive PET radionuclide (97% abundant) for radiolabeling because its 110 minute half-life allows sufficient time (3×110 minutes) for incorporation into the radiopharmaceutical and for purification of the final product suitable for human administration. Further, $^{18}F$ can be prepared in curie quantities as fluoride ion for incorporation into the radiopharmaceutical in high (theoretical 1.7 Ci/nmol) specific activity by no-carrier added nucleophilic substitution reactions. Fluorine-18 is also the lowest energy positron emitter (0.635 MeV, 2.4 mm positron range) which affords the highest resolution images. Finally the 110 minute half-life allows sufficient time for regional distribution up to a 200 mile radius from the manufacturing site. The compounds of the invention can be labeled with $^{18}F$ for the imaging of $D_2^{high}$ receptors using PET techniques.

Single photon emission computed tomography (SPECT) is a nuclear medicine tomographic imaging technique using gamma rays. It is very similar to conventional nuclear medicine planar imaging using a gamma camera, except that it is able to provide true 3D information. The technique requires injection of a gamma-emitting radioisotope into the bloodstream of the patient. Iodine-123 ($^{123}I$) is a useful SPECT radionuclide. Its half-life is 13.22 hours; the decay emits gamma radiation with predominant energies of 159 keV and 27 keV. The compounds of the invention can be labeled with $^{123}I$ for the imaging of $D_2^{high}$ receptors using SPECT techniques.

Because the compounds of the invention have high affinity for $D_2^{high}$ receptors, the specific binding of radiolabelled compound in the various regions of the subject's brain is correlated with the amount of dopamine $D_2^{high}$ receptors in that area.

The imaging methods of the invention can be used to determine if a subject is in a state of dopamine supersensitivity. The extent of dopamine supersensitivity is an important factor in the assessment of health and disease in a subject, for example, to assess, treat and/or follow the progress of any dopamine-related disorder. If a subject has elevated levels of dopamine $D_2^{high}$ receptors in their brain compared to a control, then they may be considered to have dopamine supersensitivity. Such supersensitivity affects a subject's reaction to dopamine related drugs, for example dopamine agonists, and is a significant consideration in the diagnosis and course of treatment of certain neurological conditions.

As a representative, non-limiting example, whether or not a Parkinson diseased subject is or is not sensitive to treatment with L-DOPA, or some other dopamine agonist, may depend on the number of high-affinity states of $D_2$ receptors that exist in that particular subject. Likewise, similar determinations can be useful in the treatment and diagnosis of psychoses and schizophrenia.

An alteration in the amount or density of $D_2$ receptors in the $D_2^{high}$ state in specific regions of the brain can be an indication of dopamine-related illnesses. For example, the state of dopamine supersensitivity, correlated with an elevated number of $D_2^{high}$ receptors, usually develops in early stages of dopamine-related diseases. Accordingly, the imaging methods of the invention can be used to diagnose and monitor the progression of such dopamine-related illnesses.

Formulation and Therapy

Representative examples of diseases and conditions treatable using compounds of the present invention are as listed herein above, and include, but are not limited to, Parkinson's disease, sexual dysfunction, stroke, and depressive disorders, such as major depression and bipolar disorder.

Formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

Administration of compounds in controlled release formulations is useful where the compound of the invention has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) or median toxic dose ($TD_{50}$) to median effective dose ($ED_{50}$); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticulate formulations, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Formulations for oral use also include rapidly disintegrating or dissolving dosage forms, also known as fast dissolve, fast or rapid melt, and quick disintegrating dosage forms. These dosage forms dissolve or disintegrate rapidly in the patient's mouth without chewing or the need for water within a short time frame. Because of their ease of administration, such compositions are particularly useful for the specific needs of pediatrics, geriatrics, and patients with dysphagia.

The formulations can be administered to patients in therapeutically effective amounts. For example, an amount is administered which prevents, reduces, or eliminates the symptoms of Parkinson's disease, sexual dysfunction, stroke, or depression, respectively. Typical dose ranges are from about 0.001 mg/kg to about 2 mg/kg of body-weight per day. Desirably, a dose of between 0.001 mg/kg and 1 mg/kg of body weight, or 0.005 mg/kg and 0.5 mg/kg of body weight, is administered. The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

Existing animal models can be used to establish the utility of a compound of the invention for the treatment of a particular neurological condition, such as depression or Parkinson's disease.

A symptom of clinical depression that can be modeled in rats is despair, a feeling of hopelessness. Symptoms of despair can be induced in rats using the forced swim test (FST), a highly validated model used to study antidepressant treatments. The efficacy of the compounds of the invention for the treatment of depressive disorders can be assessed using the forced swim test. The FST is a two day procedure in which rats swim under conditions in which escape is not possible. On the first day, the rats are forced to swim for 15 minutes. The rats initially search for an escape from the water, but eventually adopt a posture of immobility in which they make only the movements necessary to keep their heads above water. Upon re-testing one day later, latencies to become immobile (an indicator of how rapidly the rats "give up" in response to a familiar stressor) are decreased, which is inferred as despair. Standard antidepressants such as imipramine and fluoxetine extend latencies to become immobile. Drug efficacy in this animal model is predictive of antidepressant efficacy in humans. The FST has been described by Mague et al., J. Pharmacol. Exp. Ther. 305:323 (2003).

Selective lesions of the nigrostrial DA pathway with the neurotoxin 6-hydroxydopamine (OHDA) results in slowly evolving denervation supersensitivity of postsynaptic DA receptors in neostriatum that is believed to mimic conditions found in clinical Parkinson's Disease. When adult rats with unilateral 6-OHDA lesions are challenged with drugs that interact with DA neurotransmission, rotational behavior occurs. Indirect DA agonists, such as methylphenidate and amphetamine, that block the neuronal reuptake, induce ipsilateral rotation toward the lesioned side, whereas direct receptor agonists, such as R(−)-apomorphine, induce rotation contralateral to the lesion (U. Ungerstadt, Acta Physiol. Scand. 82:51 (1971); and U. Ungerstadt, Acta Physiol. Scand. 82:69 (1971)). These robust and quantifiable behavioral responses are believed to reflect laterally biased DA transmission caused by DA overflow in the intact side induced by indirect agonists and stimulation of supersensitized postsynaptic DA receptors in the lesioned side by direct agonists. Unilateral 6-OHDA lesioning of the nigrostriatal DA pathway can be carried out as detailed previously (see Creese et al., Science 197:596 (1977); and Zhang et al., Pharmacol. Biochem. Behav. 69:111 (2001)). In this animal model rotational behavior (turns per unit time) is an indicator of an agent's effectiveness for treating Parkinson's disease.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

General Synthetic Methods. $^1$H and $^{13}$C NMR spectra were recorded at 300 and 75 MHz, respectively using CDCl$_3$ or CD$_3$OD as solvent, on a Varian Mercury 300 spectrometer. Chemical shifts are given as δ value (ppm) downfield from tetramethylsilane as an internal reference. Melting points were determined on a Thomas-Hoover capillary tube apparatus and are reported uncorrected. Elemental analyses, performed by Atlantic Microlabs, Atlanta, Ga., were within ±0.4% of theoretical values. Analytical thin-layer chromatography (TLC) was carried out on 0 2-mm Kieselgel 60F-254 silica gel aluminum sheets (EMD Science, Newark, N.J.). Flash chromatography was used for the routine purification of reaction products.

EXAMPLE 1

Synthesis of N-(3-Fluoropropyl)-3-deoxynormorphine (5)

1-bromo-3-fluoropropane (410 mg, 2.91 mmol) was slowly added into the mixture of 3-deoxynormorphine (300 mg, 1.17 mmol) and NaHCO$_3$ (150 mg, 1.78 mmol) in EtOH (25 mL) The resulted mixture was refluxed overnight. Ethanol was removed in vacuo. Water (50 mL) was added into the residue and extracted with EtOAc (30 mL×3). The combined organic layer was washed with brine (50 mL), dried with Na$_2$SO$_4$ and evaporated in vacuo. The residue was purified on silica gel column eluting with CH$_2$Cl$_2$: MeOH=40:1 to obtain the product 5 (220 mg) in 60% yield.

EXAMPLE 2

Synthesis of Oripavine-3-triflate

Oripavine-3-triflate was prepared as described by Csutoras et al., Bioorg. Med. Chem. 12:3553 (2004) in a 98% yield (3.114g), as a crystalline, pale tan solid. Mp=138-143° C., lit value=143-145° C.

EXAMPLE 3

Synthesis of R(−)-11-Hydroxy-N-(3-fluoropropyl) noraporphine (6)

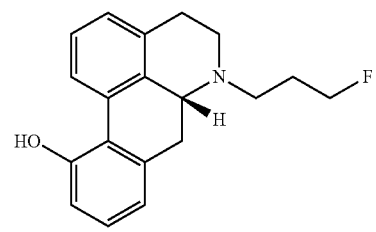

(6)

Under nitrogen atmosphere, a mixture of N-(3-fluoropropyl)-3-deoxynormorphine (5) (220 mg, 0.69 mmol) in MeSO$_3$H (8 mL) was stirred for 30 min at 95-100° C. After cooling to room temperature, the mixture was poured into ice water and brought to pH=9-10 with ammonium hydroxide. The mixture was extracted with CH$_2$Cl$_2$ (50 mL×3). The combined organic layer was washed with brine, dried with Na$_2$SO$_4$, and evaporated in vacuo. The residue was purified by silica gel column chromatography using hexanes:ethyl acetate (2:1) as eluent to afford 6 (115 mg) as a white foam in 56% yield. The free base was converted to the HCl salt with 1 M HCl in ether to afford 101 mg of a white solid. Mp. (HCl) 195-197° C. (Dec). Anal. calcd. for C$_{19}$H$_{20}$NOF.HCl.0.5H$_2$O: C, 66.49; H, 6.41; N, 4.08. Found: C, 66.68; H, 6.40; N, 4.03. $^1$H NMR (base, 300 MHz, CDCl$_3$) δ 7.97 (d, J=7.8 Hz, 1H), 7.21 (t, J=7.5 Hz, 1H), 7.03 (d, J=7.5 Hz, 1H), 6.97 (d, J=7.8 Hz, 1H), 6.77 (d, J=7.8 Hz, 1H), 6.62 (d, J=7.8 Hz, 1H), 4.62 (m, 1H), 4.46 (m, 1H), 3.36 (dd, J=13.5 and 3.0 Hz, 1H), 3.17-3.02 (m, 4H), 2.74 (dd, J=15.0 and 3.3 Hz, 1H), 2.60-2.44 (m, 3H), 2.06-1.89 (m, 2H); $^{13}$C NMR (base, 75 MHz, CDCl$_3$) δ 152.8, 138.0, 134.8, 133.1, 131.6, 127.9, 127.4, 126.2, 124.9, 121.4, 120.2, 115.6, 82.48 (d, J=163.2 Hz), 59.6, 50.09 (d, J=4.9 Hz), 48.9, 34.7, 28.9, 27.3 (d, J=19.5 Hz).

EXAMPLE 4

Synthesis of R(−)-N-propyl-2-(2-fluoropropanoxy)-10-[(trifluoromethyesulfonyl]oxy-11-hydroxynoraporphine (10a)

To a 6 dram vial under nitrogen atmosphere were added: R(−)-N-propyl-3-[(trifluoromethyl)sulfonyl]oxynororipavine (396 mg, 0.866 mmol) and fluoropropanol (300 μL). The vial was cooled to 0° C. and methanesulfonic acid (3 mL) was added. After brief stirring, the reaction was heated to 95° C. and stirred for 2 hours. After cooling, the acid solution was diluted with cold water (100 mL) and brought to pH 8-9 by dropwise addition of concentrated ammonium hydroxide solution. The aqueous phase was extracted with ethyl acetate (2×50 mL) The combined organic extracts were washed with brine, dried over magnesium sulfate, concentrated, and purified by flash column chromatography using 1:40 methanol:dichloromethane as eluent. The resulting fractions were collected and concentrated to about 10 mL, and white crystals precipitated. The crystals were filtered, washed with ether/hexanes, and dried to afford 114 mg of fine pale green needles, 26% yield. Mp (free base)=158-160° C. (dec). NMR: $^1$H NMR (300 MHz, DMSO) δ 7.28-7.11

(m, 2H), 6.95 (t, J=9.7, 1H), 6.71 (dd, J=2.3, 14.0, 1H), 4.67 (q, J=5.8, 1H), 4.51 (q, J=5.8, 1H), 4.05 (t, J=6.0, 3H), 3.15 (dd, J=12.0, 23.5, 1H), 2.86 (dd, J=10.7, 16.4, 4H), 2.68 (d, J=16.7, 1H), 2.48 (dt, J=1.8, 3.6, 2H), 2.40-2.00 (m, 2H), 1.65-1.35 (m, 2H), 0.89 (dd, J=6.5, 8.1, 3H). $^{13}$C NMR (75 MHz, DMSO) δ 157.12, 157.02, 149.46, 135.90, 135.39, 130.76, 129.35, 129.31, 129.27, 129.18, 128.52, 126.20, (118.91, q, J=329 Hz), 113.04, 81.50 (d, J=172.7), 63.99, 59.48 (d, J=10.5 Hz), 56.25, 48.96, 34.43, 30.47 (d, J=19.8), 20.03, 12.60. $^{19}$F NMR (282 MHz, DMSO) δ 8.99 (dd, J=6.4, 19.4), −74.63.

EXAMPLE 5

Synthesis of R(−)-2-(2-fluoroethoxy)-10-[(trifluoromethyl)sulfonyl]oxy-11-hydroxy-N-n-propyl-noraporphine (10b)

Under nitrogen atmosphere, a mixture of 3-O-((trifluoromethyl)sulfonyl)-N-n-propylnororipavine 9 (457 mg), MeSO$_3$H (5.0 mL) and 2-fluoroethanol (1.0 mL) was stirred for 30 min at 0° C. The mixture was warmed to rt slowly and then warmed up to 95° C. stirring for 30 min at this temperature. After cooling to room temperature, the mixture was poured into ice water and brought to pH=9-10 with ammonium hydroxide. The mixture was extracted with CH$_2$Cl$_2$ (50 mL×3). The combined organic layer was washed with brine, dried over Na$_2$SO$_4$, and evaporated in vacuo. The residue was purified by silica gel column chromatography using CH$_3$OH: CH$_2$Cl$_2$ (1:50) as eluent to afford 10 (67 mg) in 27% yield as a pale white solid. $^1$H NMR (300 MHz, CDCl$_3$) δ 7.67 (d, J=1.8 Hz, 1H), 7.12 (d, J=8.4 Hz, 1H), 6.88 (d, J=8.4 Hz, 1H), 6.77 (d, J=1.8 Hz, 1H), 4.84 (t, J=4.2 Hz, 1H), 4.68 (t, J=4.2 Hz, 1H), 4.28 (m, 1H), 4.19 (m, 1H), 3.35 (m, 1H), 3.23-3.06 (m, 2H), 2.88 (m, 1H), 2.73 (m, 1H), 2.58-2.45 (m, 2H), 1.85 (m, 2H), 1.61 (m, 2H), 0.97 (t, J=7.2 Hz, 3H).

EXAMPLE 6

Synthesis of R(−)-N-ethyl-2-(2-fluoropropanoxy)-10-[(trifluoromethyl)sulfonyl]oxy-11-hydroxynoraporphine (10c)

To a 6 dram vial under nitrogen atmosphere were added: R(−)-N-ethylnororipavine-3-trifluoromethanesulfonate (140 mg, 0.316 mmol) and fluoropropanol (70 µL) until no lumps remained. The resulting suspension was stirred for 5 minutes and then methanesulfonic acid (625 µL) and stirred art 95° C. for 1 hour. After cooling, the acidic solution was transferred to water (10 mL) and treated with concentrated ammonium hydroxide solution until pH 8-9 was reached. The resulting aqueous solution was extracted with ethyl acetate (3×5 mL), filtered through sodium sulfate, concentrated, and purified by column chromatography using 1:50 MeOH:DCM as eluent to afford 118.4 mg of a crude solid (77%; ~10% inseparable impurity present by NMR). The impure product was carried to the next step. $^1$H NMR (300 MHz, CDCl$_3$) δ 7.746 (s, 1H), 7.085 (d, 1H, J=8.01 Hz), 6.820 (d, 1H, J=7.87 Hz), 6.606 (s, 1H), 4.721 (s, 1H), 4.564 (s, 1H), 4.10-4.09 m, 2H), 3.41-3.31 (m, 1H), 3.09-3.05 (m, 4H), 2.75-2.46 (m, 4H), 2.21-2.08 (m, 2H), 1.79-1.50 (m, 1H), 1.26-1.0147 (m, 3H). $^{13}$C NMR (75 MHz, CDCl$_3$) δ 157.71, 156.94, 137.52, 134.06, 134.02, 126.80, 126.77, 124.89, 123.100 (q, J=315.4 Hz), 119.96, 115.75, 113.14, 112.56, 80.67 (d, J=164.1 Hz), 63.40 (d, J=4.9 Hz), 58.09, 55.10, 47.59 (d, J=19.3 Hz), 34.35, 29.54, 28.58, 10.11. $^{19}$F NMR (282 MHz, CDCl$_3$) 7.223 (tt, J=48.54, 24.89 Hz).

EXAMPLE 7

Synthesis of R(−)-N-ethyl-2-(2-fluoroethoxy)-10-[(trifluoromethyesulfonyl]oxy-11-hydroxynoraporphine (10d)

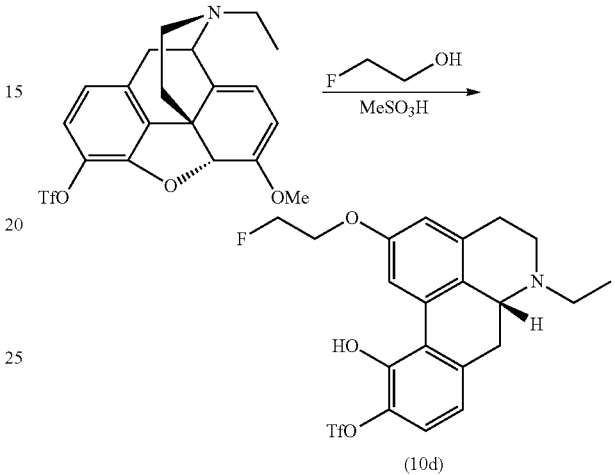

(10d)

To a 6 dram vial under nitrogen atmosphere were added: R(−)-N-ethyl-3-trifluoromethylsulfonyloxynororipavine (119 mg, 0.268 mmol) and fluoroethanol (60 µL). The vial was cooled to 0° C. and methanesulfonic acid (0.53 mL) was added. After brief stirring, the reaction was heated to 95° C. and stirred for 30 minutes. After cooling, the acid solution was diluted with cold water (50 mL) and brought to pH 8-9 by dropwise addition of concentrated ammonium hydroxide solution. The aqueous phase was extracted with ethyl acetate (2×50 mL) and with dichloromethane (1×40 mL) The combined organic extracts were washed with brine, dried over sodium sulfate, concentrated, and purified by flash column chromatography using 1:15 methanol:dichloromethane as eluent. The resulting fractions were collected and concentrated to about 10 mL, and white crystals precipitated. After storing it in the freezer overnight, the crystals were filtered and dried to afford 58 mg of R(−)-N-ethyl-3-trifluoromethylsulfonyloxy-noraporphine fine white needles, 44% yield. Mp (free base)=171-173° C. (dec). NMR: $^1$H NMR (300 MHz, DMSO) δ 7.21 (dd, J=5.3, 13.4, 2H), 6.96 (t, J=10.0, 1H), 6.81-6.65 (m, 1H), 4.89-4.72 (m, 1H), 4.64 (t, J=3.8, 1H), 4.34-4.05 (m, 2H), 3.17-2.83 (m, 5H), 2.72 (d, J=16.0, 2H), 2.44-2.08 (m, 2H), 1.06 (t, J=5.8, 3H). $^{19}$F NMR (282 MHz, DMSO) δ −43.99−−47.06 (m), −74.12, −74.52. The product contains an inseparable trace of the 2-methoxy analog (reflected in a $^{19}$F shift corresponding to the 2-MeO byproduct).

EXAMPLE 8

Synthesis of R(−)-2-(2-fluoroethoxy)-10-((trifluoromethyl)sulfonyl)oxy-11-hydroxyaporphine (10g)

To a 25 mL round bottomed flask was added oripavine-3-triflate (1.0 g, 2.33 mmol). The flask was flushed with nitrogen and put on ice. Next, 2-fluoroethanol (1.0 mL) was added, followed by methanesulfonic acid (5.5 mL) The mixture was stirred briefly at 0° C., then heated at 90-95° C. while stirring for 40 minutes. After cooling, the mixture was transferred dropwise to ice water (100 mL) while stirring. The aqueous mixture was basified with ammonium hydroxide solution, then extracted with dichloromethane (2×30 mL) The organic extracts were combined, washed with brine, concentrated, and purified over silica gel using 1:20 methanol:dichloromethane eluent (which was not adequate for purification). The resulting solid was then recrystallized from methanol and then the mother liquor was concentrated and the title compound was recrystallized again from DCM/ether to afford 579 mg of the product as fine grey-green needles (54% yield), containing about 11% by mol of a 2-methoxy analog as an inseparable impurity. $^1$H NMR (300 MHz, DMSO) δ 7.70 (s, 1H), 7.25 (d, J=8.2, 2H), 6.98 (s, 1H), 6.77 (d, J=15.4, 1H), 4.74 (d, J=47.9, 2H), 4.22 (d, J=27.5, 2H), 3.76 (s, 0.3H), 3.27-3.11 (m, 2H), 2.96 (s, 3H), 2.75-2.71 (m, 1H), 2.45 (s, 3H), 2.42-2.13 (m, 1H). $^{19}$F NMR (282 MHz, DMSO) δ 7.72-7.20 (m), −74.16, −74.53.

EXAMPLE 9

Synthesis of R(−)-2-(2-fluoropropanoxy)-11-hydroxy-N-n-propylnoraporphine (11a)

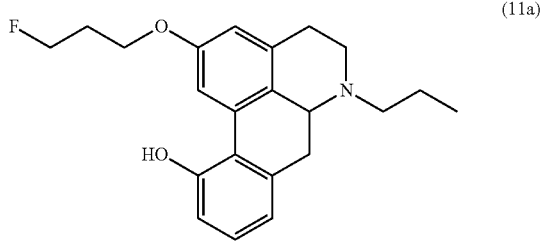 [SMILES: CCCN1CCc2cc(OCCCF)cc3c2C1Cc1cccc(O)c1-3]

(11a)

To a 6 dram vial containing R(−)-N-ethyl-2-fluoropropanoxy-11-hydroxy-10-trifluoromethylsulfonyloxy-noraporphine (118 mg, 0.214 mmol) was equipped with a spin vane and evacuated and flushed with dry nitrogen (3 cycles). Next, 10% palladium on carbon (19 mg), magnesium turning (19 mg), and ammonium acetate (90 mg) were loaded and the vial was evacuated and flushed with dry nitrogen (3 cycles). Next, anhydrous methanol (6.4 mL) was added and the contents were stirred overnight. The next day, the reaction was quenched by adding a few drops of ammonium hydroxide solution, then filtered through a pad of silica gel and washed with two volumes of methanol. The filtrate was concentrated and purified by flash column chromatography using 1:80 to 1:40 to 1:20 to 1:10 methanol:dichloromethane gradient to afford 72 mg of a mixture of R(−)-N-propyl-2-fluoropropanoxy-11-hydroxynoraporphine in 95% yield as a greenish glass. The compound was converted to its hydrochloride salt using ethereal HCl. Mp=150-153° C. (decomposed). $^1$H NMR (300 MHz, CDCl$_3$) δ 7.72 (d, J=2.5, 1H), 7.06-6.91 (m, 1H), 6.78 (d, J=7.4, 1H), 6.67 (d, J=8.0, 1H), 6.57 (t, J=3.1, 1H), 4.70 (t, J=5.8, 1H), 4.54 (t, J=5.8, 1H), 4.06 (t, J=6.1, 3H), 3.77 (s, 1H), 3.42-2.85 (m, 3H), 2.76-2.40 (m, 4H), 2.22-2.06 (m, 2H), 1.74-1.49 (m, 2H), 0.95 (t, J=7.3, 3H). $^{13}$C NMR (75 MHz, CDCl$_3$) δ 156.95, 153.27, 138.37, 134.25, 132.94, 128.01, 127.52, 121.23, 120.19, 115.64, 112.64, 112.13, 80.85 (d, J=164.2), 63.36 (d, J=5.3), 59.12, 56.25, 48.91, 34.99, 30.38 (d, J=19.9), 29.11, 18.84, 12.07. $^{19}$F NMR (282 MHz, CDCl$_3$) δ 7.82 (td, J=23.6, 47.2).

Alternatively, to a 6 dram vial under nitrogen atmosphere were added: R(−)-2-fluoropropanoxy-11-hydroxy-10-trifluoromethanesulfonyloxyaporphine (70 mg, 0.197 mmol), palladium on carbon (17 mg), magnesium turnings (14 mg), and ammonium acetate (74 mg). The vial was then capped and evacuated and flushed with nitrogen (3 cycles) and anhydrous methanol was added (6 mL) The resulting suspension was then stirred at room temperature for 1 day. After the reaction was judged complete by TLC, the reaction was quenched by adding triethylamine (0 5 mL), filtered through a pad of Celite, and washed with two portions of methanol. The methanol solution was then concentrated and loaded onto silica gel and purified by column chromatography using 1:10 methanol:dichloromethane to afford 15.2 mg of product as a brown foam (0.0428 mmol, 22% yield). EA calcd (C$_{22}$H$_{26}$FNO$_2$·¾H$_2$O): C, 71.91; H, 7.50; N, 3.80. Found: C, 71.30; H, 7.43; N, 3.80. $^1$H NMR (300 MHz, CDCl$_3$) δ 7.63 (d, J=2.4, 1H), 7.05 (t, J=7.7, 1H), 6.84 (d, J=7.3, 1H), 6.74 (d, J=7.8, 1H), 6.60 (s, 1H), 4.72 (t, J=5.8, 1H), 4.56 (t, J=5.8, 1H), 4.09 (t, J=6.1, 2H), 3.80 (s, 1H), 3.32 (d, J=13.1, 1H), 3.12 (m, 3H), 2.90 (s, 1H), 2.71 (d, J=15.9, 1H), 2.48 (m, 3H), 2.14 (ddd, J=5.9, 11.8, 23.7, 2H), 1.63 (dd, J=9.2, 15.8, 2H), 0.96 (t, J=7.3, 3H). $^{13}$C NMR (75 MHz, CDCl$_3$) δ 157.06, 152.83, 138.68, 134.87, 132.70, 128.17, 128.11, 121.26, 120.55, 115.58, 112.68, 111.94, 80.85 (d, J=164.1), 63.48 (d, J=5.3), 59.23, 56.45, 49.04, 35.31, 30.45 (d, J=19.9), 29.50, 19.32, 12.10. $^{19}$F NMR (282 MHz, CDCl$_3$) δ 7.65 (tt, J=25.9, 47.1).

EXAMPLE 10

Synthesis of R(−)-2-(2-fluoroethoxy)-11-hydroxy-N-n-propylnoraporphine (11b)

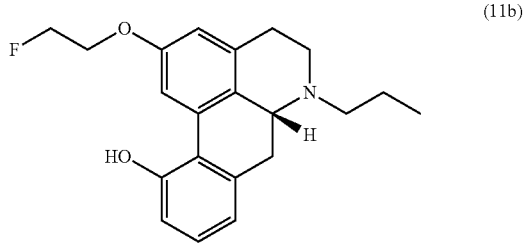 [SMILES: CCCN1CCc2cc(OCCF)cc3c2[C@H]1Cc1cccc(O)c1-3]

(11b)

Under nitrogen atmosphere, Mg (9 mg, 0.38 mmol) and NH$_4$OAc (45 mg, 0.58 mmol) was added to the mixture of R(−)-2-(2-fluoroethoxy)-10-((trifluoromethyl)sulfonyl)oxy-11-hydroxy-N-n-propyl-noraporphine 10 (65 mg, 0.14 mmol) and 10% Pd/C (13 mg) in MeOH (5.0 mL) The resulted mixture was stirred at rt for 24 hr and filtered with celite. The filtration was evaporated to dryness and dissolved in CH$_2$Cl$_2$. The solution was washed with 10% NH$_4$OH and brine. The solution was dried with Na$_2$SO$_4$ and evaporated in vacuo to dryness. The residue was purified on column eluting with CH$_2$Cl$_2$: MeOH=100:1 obtaining R(−)-2-(2-fluoroethoxy)-11-hydroxy-N-n-propylnoraporphine (37 mg) as oil. The free base was converted to the HCl salt with 1N HCl in ether as white solid. Mp. (HCl salt) 168-170° C. (Dec). Anal. calcd. for C$_{20}$H$_{23}$NO.HCl.0.5H$_2$O: C, 65.13; H, 6.46; N, 3.61. Found: C, 64.78; H, 6.69; N, 3.51. $^1$H NMR (base, 300 MHz, CDCl$_3$) δ 8.17 (br, 1H), 7.80 (d, J=2.4 Hz, 1H), 6.96 (t, J=7.5 Hz, 1H), 6.76 (d, J=8.1 Hz, 1H), 6.70 (d, J=7.2 Hz, 1H), 6.53 (d, J=2.4 Hz, 1H), 4.75 (t, J=3.9 Hz, 1H), 4.59 (t, J=3.9 Hz, 1H), 4.17 (m, 1H), 4.08 (m, 1H), 3.53 (m, 1H), 3.30-3.25 (m, 1H), 3.13-2.86 (m, 3H), 2.70-2.53 (m, 4H), 1.70-1.57 (m, 2H), 0.94 (t, J=6.9 Hz, 3H); $^{13}$C NMR (base, 75 MHz, CDCl$_3$) δ 156.7, 153.7, 137.4, 133.3, 128.2, 120.6, 119.9, 115.8, 112.7, 112.5, 81.9 (d, J=169.4 Hz), 67.0 (d, J=20.1 Hz), 59.0, 48.2, 34.3, 29.6, 27.9, 18.5, 11.8. $^{19}$F NMR (base, 282 MHz, CDCl$_3$) δ 6.02 (tt, J=47.5, 28.1 Hz).

EXAMPLE 11

Synthesis of R(−)-2-(2-fluoropropanoxy)-11-hydroxy-N-n-ethylnoraporphine (11c)

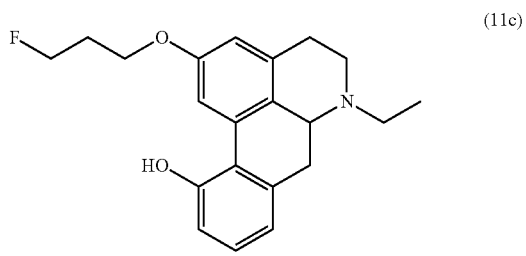 [SMILES: CCN1CCc2cc(OCCCF)cc3c2C1Cc1cccc(O)c1-3]

(11c)

To a 6 dram vial under nitrogen atmosphere was added: R(−)-N-ethyl-2-fluoropropanoxy-11-hydroxy-10-trifluoromethylsulfonyloxyaporphine (118 mg, 0.242 mmol), Pd(OAc)$_2$ (16 mg, 10%), and dppp (11 mg, 10%). The vial was capped and evacuated and flushed with nitrogen 3 times. Next, anhydrous DMF (1.5 mL) was added, followed by triethylhydrosilane (100 μL). After brief stirring at RT, the mixture was heated at 60° C. for 4 hours. The reaction mixture was quenched by removing DMF under reduced pressure, dissolving the residue in dichloromethane (50 mL), and washing with 28% ammonium hydroxide solution (15 mL) The residue was purified 3× by column chromatography using 1:30 to 1:10 MeOH to DCM gradient to afford 24 mg of the desired product (27% yield) and 33 mg of an undesired unidentified byproduct. The title product was converted to the HCl salt by treatment with excess ethereal HCl. Mp (HCl salt)=156-158° C. (decomposed). EA: C$_{21}$H$_{24}$FNO$_2$.½ H$_2$O Anal. Calcd.: C, 71.98; H, 7.19; N, 4.00. EA: C$_{21}$H$_{24}$FNO$_2$.0.38CH$_3$OH.0.063CH$_2$Cl$_2$ Anal. Calcd.: C, 71.75; H, 7.20; N, 3.90. Found: C, 71.99; H, 7.19; N, 3.89. (free base) $^1$H NMR (300 MHz, CDCl$_3$) δ 7.674 (s, 1H), 7.021 (t, 1H, J=7.69 Hz), 6.798 (d, 1H, J=7.25 Hz), 6.710 (d. 1H, J=8.00 Hz), 6.584 (s, 1H), 4.708 (t, 1H, J=5.76 Hz), 4.551 (t, 1H, J=5.73 Hz), 4.077 (t, 2H, J=6.00 Hz), 3.372 (d, 1H, J=14.05 Hz), 3.19-3.05 (m, 4H), 2.75-2.49 (m, 4H), 2.139 (dt, 2H, J=25.82, 5.89 Hz), 1.170 (t, 3H, J=7.02 Hz). $^{13}$C NMR (75 MHz, CDCl$_3$) δ 157.71, 156.94, 139.13, 137.52, 134.06, 134.02, 126.80, 126.77, 124.89, 119.96, 119.63, 115.75, 113.14, 112.56, 112.01, 80.67 (d, J=164.1 Hz), 63.40 (d, J=4.9 Hz), 58.09, 55.10, 47.59 (d, J=19.3 Hz), 34.35, 29.54, 28.58, 10.11. $^{19}$F NMR (282 MHz, CDCl$_3$) δ 7.673 (tt, J=48.24, 24.64 Hz).

EXAMPLE 12

Synthesis of R(−)-2-(2-fluoroethoxy)-11-hydroxy-N-n-ethylnoraporphine (11d)

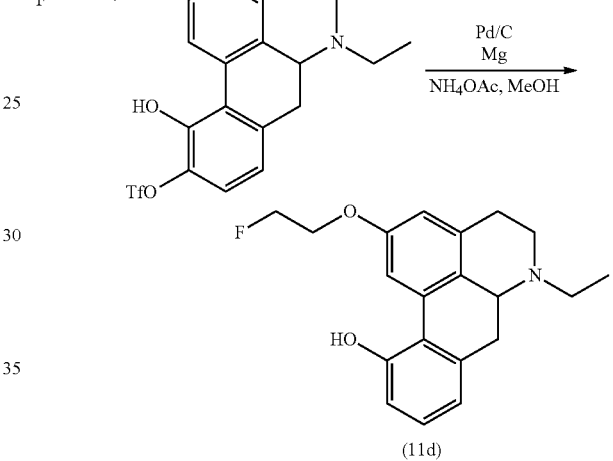

(11d)

To a 6 dram vial containing R(−)-N-ethyl-2-fluoroethoxy-11-hydroxy-10-trifluoromethylsulfonyloxy-noraporphine (140 mg, 0.286 mmol) was equipped with a spin vane and evacuated and flushed with dry nitrogen (3 cycles). Next, 10% palladium on carbon (45 mg), magnesium turning (21 mg), and ammonium acetate (88 mg) were loaded and the vial was evacuated and flushed with dry nitrogen (3 cycles). Next, anhydrous methanol (8 mL) was added and the contents were stirred overnight. The next day, the reaction was quenched by adding a few drops of ammonium hydroxide solution, then filtered through a pad of silica gel and washed with two volumes of methanol. The filtrate was concentrated and purified by flash column chromatography using 1:30 to 1:20 methanol:dichloromethane gradient to afford 55 mg slightly green foam as product, yield 57%. The free base was converted to HCl salt. $^1$H NMR (300 MHz, CDCl$_3$) δ 7.73 (d, J=2.5, 1H), 7.02 (t, J=7.7, 1H), 6.79 (d, J=7.3, 1H), 6.70 (d, J=8.1, 1H), 6.60 (d, J=2.3, 1H), 4.77 (m, 1H), 4.62 (m, 1H), 4.20 (m, 1H), 4.11 (m, 1H), 3.38 (m, 1H), 3.12 (m, 4H), 2.59 (m, 4H), 1.17 (t, J=7.1, 3H). $^{13}$C NMR (75 MHz, CDCl$_3$) δ 156.62, 153.31, 138.41, 134.46, 132.98, 128.10, 128.07, 121.18, 120.20, 115.67, 113.03, 112.01, 82.03 (d, J=169.5 Hz), 67.04 (d, J=20.2 Hz), 58.54, 48.06, 47.85, 34.92, 29.19, 10.46. M.P. (HCl salt)>168° C. Anal. Calc. for C$_{20}$H$_{22}$FNO$_2$ xHClx0.6H$_2$O, C, 64.11; H, 6.51; N, 3.74. Found: C, 64.02, H, 6.54; N, 3.76.

EXAMPLE 13

Synthesis of R(-)-2-(2-fluoroethoxy)-11-hydroxy-aporphine (11g)

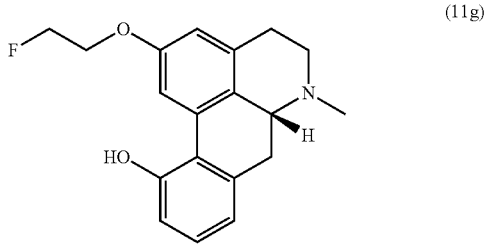 [SMILES: CN1CCc2cc(OCCF)cc3c2[C@H]1Cc1cccc(O)c1-3]

(11g)

To a 100 mL round bottomed flask were sequentially added: R(-)-2-(2-fluoroethoxy)-11-hydroxy-3-[(trifluoromethyl)sulfonyl]oxyaporphine (300 mg), palladium on carbon (10%, 57 mg), magnesium turnings (50 mg), and ammonium acetate (252 mg). The flask was flushed with dry nitrogen and anhydrous methanol (20 mL) was added. The mixture was allowed to stir for 24 hours, until judged complete by TLC. The contents were filtered through a plug of Celite, which was washed with methanol (2×20 mL), and concentrated. The residue was dissolved in dichloromethane and methanol and adsorbed onto silica gel, and the solvents were removed under reduced pressure. The product was purified from the silica gel by column chromatography using 1:15 methanol:dichloromethane as eluent to afford 119 mg of R(-)-2-fluoroethoxy-11-hydroxyaporphine as a glassy green film in 58% isolated yield. The free base was then dissolved in methanol and treated with ethereal hydrogen chloride to afford 111 mg of the corresponding hydrochloride salt as a pale tan solid. Mp (HCl salt): 184-188° C. (decomposed). EA: $C_{19}H_{19}NO_2F\cdot HCl\cdot \frac{2}{3}H_2O$: calcd: C, 63.07; H, 6.22; N, 3.87. Found: C, 63.12; H, 6.15; N, 3.89. $^1H$ NMR (300 MHz, CD3OD) δ 7.80 (d, J=2.6, 1H), 6.94-6.81 (m, 1H), 6.66 (d, J=7.9, 1H), 6.60 (d, J=7.3, 1H), 6.43 (d, J=2.5, 1H), 4.69-4.57 (m, 1H), 4.51-4.42 (m, 1H), 4.10-4.01 (m, 1H), 4.00-3.88 (m, 1H), 3.28-3.14 (m, 1H), 3.01-2.79 (m, 4H), 2.51 (dd, J=3.5, 16.5, 1H), 2.33 (s, 3H), 2.39-2.24 (m, 1H). $^{13}C$ NMR (75 MHz, CD3OD) δ 157.10, 154.69, 137.67, 133.54, 133.23, 128.10, 126.68, 120.73, 119.58, 115.26, 113.69, 111.97, 82.07 (d, J=168.9 Hz), 67.28 (d, J=19.9 Hz), 62.06, 52.90, 42.68, 34.86, 28.68. $^{19}F$ NMR (282 MHz, CD3OD) δ 4.67 (tt, J=29.0, 47.9 Hz).

EXAMPLE 14

General Procedure for the Preparation of R(-)-2-Fluoroalkoxy-N-alkyl-10,11-dihydroxy aporphines 8a-d, f, g A mixture of N-alkylnororipavine 7a-d or oripavine (0.27 mmol), MeSO3H (2.5 mL) and fluoroalkyl alcohol (0 5 mL) was stirred for 30 min at 0° C. The mixture was warmed to rt slowly and then warmed up to 95° C. stirring for 30 min at this temperature. After cooling to room temperature, the mixture was poured into ice water and basified to pH=9-10 with ammonium hydroxide. The mixture was extracted with CH2Cl2 (50 mL×3). The combined organic layer was washed with brine, dried with Na2SO4, and evaporated in vacuo. The residue was purified on silica gel column eluting with CH3OH: CH2Cl2=1:50 obtaining 8a-d,f,g in 6-47% yields. The free bases were converted to HCl salts with 1N HCl in ether.

EXAMPLE 15

R(-)-2-(3-fluoropropanoxy)-NPA (8a)

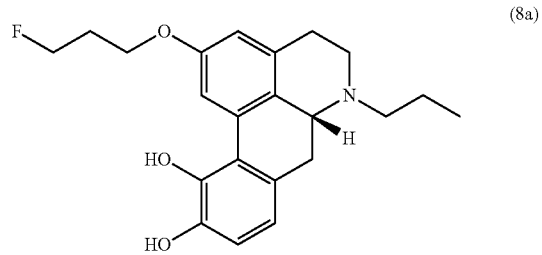 [SMILES: CCCN1CCc2cc(OCCCF)cc3c2[C@H]1Cc1ccc(O)c(O)c1-3]

(8a)

6%. Mp. (HCl salt) 180-182° C. Anal. calcd. for $C_{22}H_{26}NFO_3\cdot HCl$: C, 64.78; H, 6.67; N, 3.42. Found: C, 64.54; H, 6.67; N, 3.02. $^1H$ NMR (base, 300 MHz, CDCl3) δ 7.83 (d, J=2.4 Hz, 1H), 6.56 (d, J=7.6 Hz, 1H), 6.53 (d, J=2.4 Hz, 1H), 6.47 (d, J=7.6 Hz, 1H), 5.6 (br, 2H), 4.72 (t, J=6.0 Hz, 1H), 4.55 (t, J=6.0 Hz, 1H), 4.10-4.01 (m, 2H), 3.40 (m, 1H), 3.24-3.04 (m, 2H), 2.90-2.81 (m, 2H), 2.70-2.50 (m, 4H), 2.22-1.98 (m, 2H), 1.70-1.61 (m, 2H), 0.94 (t, J=7.2 Hz, 3H); $^{13}C$ NMR (base, 75 MHz, CDCl3) δ 157.2, 143.8, 143.0, 133.5, 133.1, 127.8, 120.2, 118.8, 114.0, 112.8, 112.4, 80.5 (d, J=163.1 Hz), 63.3 (d, J=5.4 Hz), 59.4, 54.9, 48.4, 33.87, 30.3 (d, J=20.1 Hz), 27.9, 18.4, 11.9.

EXAMPLE 16

R(-)-2-Fluoroethyoxy-NPA (8b)

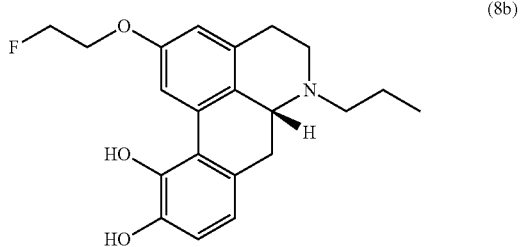 [SMILES: CCCN1CCc2cc(OCCF)cc3c2[C@H]1Cc1ccc(O)c(O)c1-3]

(8b)

47%. Mp. (HCl salt) 203-205° C. (Dec.). Anal. calcd. for $C_{21}H_{24}NFO_3\cdot HCl\cdot 1.25H_2O$: C, 60.64; H, 6.61; N, 3.36. Found: C, 60.52; H, 6.47; N, 3.15. $^1H$ NMR (base, 300 MHz, CDCl3) δ 7.84 (d, J=2.4 Hz, 1H), 7.64 (br, s, 2H), 6.51 (d, J=2.4 Hz, 1H), 6.49 (s, 2H), 4.78 (t, J=4.2 Hz, 1H), 4.62 (t, J=4.2 Hz, 1H), 4.18 (m, 1H), 4.11 (m, 1H), 3.39 (m, 1H), 3.19-3.07 (m 2H), 2.96-2.83 (m, 2H), 2.68-2.48 (m, 4H), 1.63-1.55 (m, 2H), 0.93 (t, J=6.9 Hz, 3H); $^{13}C$ NMR (base, 75 MHz, CDCl3) δ 156.7, 144.0, 143.2, 133.5, 127.8, 126.5, 120.2, 118.8, 114.0, 112.7, 81.9 (d, J=169.1 Hz), 67.0 (d, J=20.3 Hz), 59.3, 55.5, 48.6, 33.8, 28.3, 18.2, 12.0.

EXAMPLE 17

R(−)-2-(3-Fluoropropanoxy) 10,11-dihydroxy-N-ethylnoraporphine (8c)

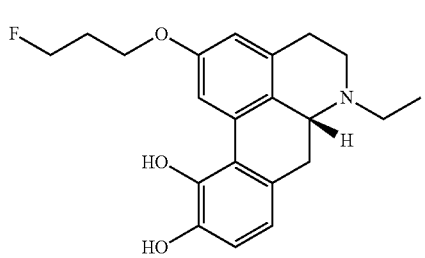

36%. Mp. (HCl salt). 174-176° C. (Dec.). Anal. calcd. for $C_{21}H_{24}NFO_3 \cdot HCl \cdot H_2O$: C, 61.24; H, 6.61; N, 3.40. Found: C, 61.52; H, 6.40; N, 3.38. $^1$H NMR (base, 300 MHz, CDCl$_3$) δ 7.80 (d, J=2.6, 1H), 6.62-6.46 (m, 3H), 4.72 (t, J=5.8, 1H), 4.56 (t, J=5.8, 1H), 4.09-4.06 (m, 2H), 3.49-3.46 (m, 1H), 3.25-2.85 (m, 4H), 2.79-2.61 (m, 2H), 2.52 (t, J=13.6, 2H), 2.27-2.01 (m, 2H), 1.16 (t, J=7.1, 3H). $^{13}$C NMR (base, 75 MHz, CDCl$_3$) δ 157.91, 157.08, 143.43, 142.77, 133.80, 133.28, 128.54, 126.71, 120.49, 118.91, 113.81, 112.60, 80.9 (d, J=163.5 Hz), 63.38 (d, J=5.3 Hz), 58.80, 55.19, 47.58 (d, J=40.0 Hz), 34.00, 30.52, 30.26, 28.60, 10.11. $^{19}$F NMR (base, 282 MHz, CDCl$_3$) δ 7.69 (tt, J=25.9, 47.2 Hz).

EXAMPLE 18

R(−)-2-fluoroethoxy-N-ethylnorapomorphine (8d)

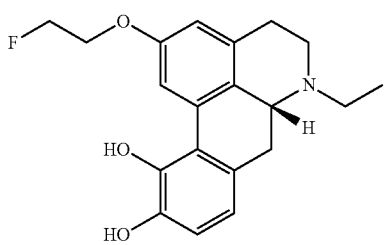

32%. Mp. (HCl salt) 163-165° C. Anal. calcd. for $C_{20}H_{22}NFO_3 \cdot HCl \cdot 0.75H_2O$: C, 61.07; H, 6.28; N, 3.56. Found: C, 60.94; H, 6.18; N, 3.63. $^1$H NMR (salt, 300 MHz, CD$_3$OD) δ 8.08 (dd, J=2.6, 6.3, 1H), 6.85-6.62 (m, 3H), 4.82 (ddd, J=1.2, 2.3, 4.1, 1H), 4.66 (dd, J=3.2, 4.7, 1H), 4.28-4.20 (m, 3H), 3.91-3.74 (m, 2H), 3.45-3.25 (m, 5H), 3.20-3.05 (m, 1H), 2.75 (t, J=13.7, 1H), 1.45 (t, J=7.3, 3H). $^{13}$C NMR (salt, 75 MHz, CD$_3$OD) δ 159.45, 158.33, 145.02, 143.47, 134.43, 130.97, 124.45, 124.43, 121.01, 118.84, 114.83, 114.20, 114.11, 111.61, 82.01 (d, J=168.0 Hz), 67.41, 60.48, 60.42, 54.59, 31.54 (d, J=5.5 Hz), 26.18, 7.91. 19F NMR (salt, 282 MHz, CD3OD) δ 4.29 (tt, JCF=28.9, 47.9 Hz).

EXAMPLE 19

R(−)-2-(3-Fluoropropanoxy) 10,11-dihydroxyaporphine (8f)

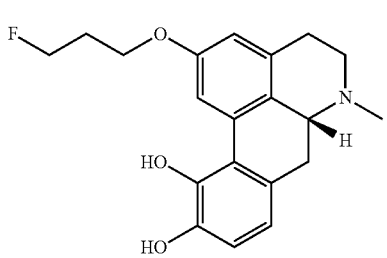

3.6 mmol scale; 28% isolated yield. Mp(HCl salt)=170-175° C. (decomposed). EA: Anal. calcd. for $C_{20}H_{22}FNO_3 \cdot HCl \cdot \frac{1}{3}H_2O$: C, 61.77; H, 6.22; N, 3.60. Found: C, 61.95; H, 6.08; N, 3.57. NMR: $^1$H NMR(HCl salt) (300 MHz, CD3OD) δ 8.08 (d, J=2.5, 1H), 6.82-6.60 (m, 3H), 4.71 (t, J=5.8, 1H), 4.55 (t, J=5.8, 1H), 4.13 (t, J=6.2, 2H), 3.79-3.70 (m, 1H), 3.52-3.35 (m, 2H), 3.31 (s, 3H), 3.20-3.01 (m, 5H), 2.76 (t, J=13.6, 1H), 2.21 (p, J=6.0, 1H), 2.12 (p, J=6.1, 1H). $^{13}$C NMR (75 MHz, CD3OD) δ 158.78, 145.11, 143.65, 134.27, 130.49, 124.33, 119.54, 118.81, 114.75, 114.07, 111.93, 111.28, 81.55, 79.38, 63.67, 63.60, 62.84 (dd, JC-F=6.9, 14.5 Hz), 31.77, 30.45, 30.19. $^{19}$F NMR (282 MHz, CD3OD) δ 5.57 (tt, J=25.6, 47.3 Hz).

EXAMPLE 20

R(−)-2-(2-Fluoroethoxy) 10,11-dihydroxyaporphine (8g)

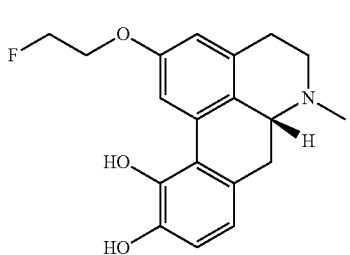

29%. Mp=236-238° C. (decomposed). EA: Anal. calcd. for $C_{19}H_{20}FNO_3 \cdot HCl$: C, 62.38; H, 5.79; N, 3.77. Found: C, 62.12; H, 5.86; N, 3.77. $^1$H NMR (300 MHz, CD3OD) δ 8.10 (d, J=2.6, 1H), 6.77-6.66 (m, 3H), 4.84-4.79 (m, 1H), 4.69-4.62 (m, 1H), 4.33-4.26 (m, 1H), 4.22-4.17 (m, 1H), 3.82 (s, 1H), 3.77 (dd, J=4.3, 11.0, 1H), 3.56-3.39 (m, 2H), 3.31 (s, 3H), 3.15 (s, 2H), 3.09 (d, J=3.4, 1H), 2.76 (t, J=13.3, 1H). $^{13}$C NMR (75 MHz, CD3OD) δ 159.64, 158.54, 145.13, 143.69, 134.36, 124.31, 118.80, 114.80, 114.10, 114.03, 111.96, 111.29, 83.06, 80.82, 67.56, 67.29, 63.06-62.73 (m, JC F), 54.57, 31.75. $^{19}$F NMR (282 MHz, CD3OD) δ 4.27 (tt, J=28.8, 47.8, 1H).

EXAMPLE 21

Synthesis of R(−)-2-iodoethoxy-N-ethylnorapomorphine (8e)

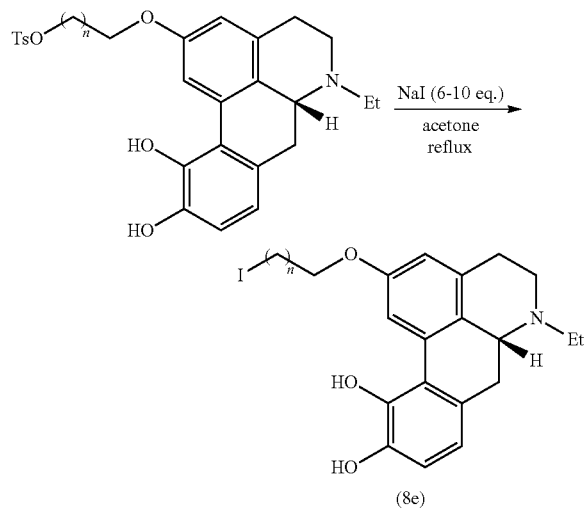

(8e)

R(−)-2-Tosyloxyethoxy-10,11-hydroxy-N-ethylnoraporphine hydrochloride 15c (61.5 mg; 0.116 mmol) was dissolved in methanol and dichloromethane, and treated with ammonium hydroxide solution to free the base. The solution was concentrated and the residue was dissolved in dichloromethane. The organic layer was filtered through sodium sulfate, concentrated, and redissolved in acetone (20 mL) and transferred to a 50 mL flask. Next, sodium iodide was added (150 mg, 1 mmol 10 equiv), and the flask was fitted with a stir bar, condenser, flushed with nitrogen, and fitted with a nitrogen balloon. The mixture was allowed to reflux overnight, until judged complete by TLC, which indicated formation of a single product. The solution was then filtered through sodium sulfate, concentrated, and purified over silica gel using 1:10 MeOH:DCM as eluent to afford pure R(−)-2-iodoethoxy-10,11-hydroxy-N-ethylnoraporphine 8e. The product was then dissolved in dichloromethane and converted to its hydrochloride salt by treatment with ethereal HCl (1M) to afford the salt in 24% isolated yield (15.8 mg). M.p. (HCl salt)=155-163° C. (decomposed). EA: Anal. calcd. for $C_{20}H_{22}INO_3 \cdot HCl \cdot 3/4H_2O$: C, 47.92; H, 4.93; N, 2.79. Found: C, 48.14; H, 4.90; N, 2.62. NMR: $^1$H NMR (300 MHz, CD3OD) δ 8.10-8.02 (m, 1H), 6.80-6.70 (m, 3H), 4.35-4.12 (m, 2H), 3.81 (d, J=37.6, 3H), 3.50 (t, J=5.9, 2H), 3.33 (s, 3H), 3.12-3.05 (m, 2H), 2.75 (t, J=13.3, 1H), 1.50-1.43 (m, 3H). $^{13}$C NMR (75 MHz, CD3OD) δ 157.98, 145.12, 143.57, 134.52, 130.95, 124.45, 121.16, 119.50, 118.84, 114.76, 114.17, 112.19, 70.26, 68.81, 60.52, 48.81, 31.57, 26.21, 7.95, 0.60.

EXAMPLE 22

Synthesis of R(−)-2-(2-p-Toluenesulfonyloxy)ethoxy-NPA (15b)

A mixture of N-n-propylnororipavine (460 mg, 1.4 mmol), MeSO$_3$H (5.0 mL) and 2-p-tosyloxyethanol (1.0 g) was stirred for 30 min at 0° C. The mixture was warmed to rt slowly and then warmed up to 95° C. stirring for 30 min at this temperature. After cooling to room temperature, the mixture was poured into ice water and basified to pH=9-10 with ammonium hydroxide. The mixture was extracted with CH$_2$Cl$_2$ (50 mL×3). The combined organic layer was washed with brine, dried with Na$_2$SO$_4$, and evaporated in vacuo. The residue was purified on silica gel column eluting with CH$_3$OH: CH$_2$Cl$_2$=1:10 (R$_f$=0.5) obtaining 12b (42 mg) in 8% yield pale white foam. The free base was converted to HCl salt with 1N HCl in ether. $^1$H NMR (300 MHz, CDCl$_3$) δ 7.78 (d, J=8.2 Hz, 2H), 7.69 (d, J=2.0 Hz, 1H), 7.28 (d, J=8.2 Hz, 2H), 6.52 (s, 2H), 6.38 (d, J=2.0 Hz, 1H), 5.33 (br, s, 2H), 4.30 (t, J=4.5 Hz, 2H), 4.08 (m, 2H), 3.35 (m, 1H), 3.19-3.07 (m, 2H), 2.96-2.83 (m, 2H), 2.66-2.46 (m, 4H), 2.37 (s, 3H), 1.63-1.60 (m, 2H), 0.93 (t, J=7.2 Hz, 3H); $^{13}$C NMR (base, 75 MHz, CDCl$_3$) δ 156.3, 144.9, 143.7, 143.0, 133.6, 133.4, 132.6, 129.8, 128.1, 127.9, 126.9, 120.2, 118.8, 113.9, 112.6, 68.3, 65.3, 59.3, 55.5, 50.6, 48.6, 33.9, 21.5, 18.4, 11.9.

EXAMPLE 23

Synthesis of R(−)-N-Ethyl-2-(2-p-toluenesulfonyloxy)-ethoxynoraporphine (15c)

2.24 mmol scale; 17.5% isolated yield. Mp (HCl salt)=134° C. EA: $C_{26}H_{27}NO_6S \cdot HCl \cdot 1/3H_2O$: Anal. calcd. C, 60.27; H, 5.74; N, 2.60. Found: C, 60.07; H, 5.74; N, 2.58. $^1$H NMR (300 MHz, CDCl$_3$) δ 7.76 (d, J=8.3, 2H), 7.70 (d, J=2.0, 1H), 7.30-7.23 (m, 2H), 6.47 (dd, J=8.0, 16.1, 2H), 6.33 (s, 1H), 4.26 (d, J=4.1, 2H), 4.17-3.93 (m, 2H), 3.36 (d, J=13.0, 1H), 3.26-2.97 (m, 3H), 2.90 (d, J=10.9, 1H), 2.56 (dt, J=13.4, 25.5, 5H), 2.35 (s, 3H), 1.14 (t, J=6.9, 3H). $^{13}$C NMR (75 MHz, CDCl$_3$) δ 156.61, 145.21, 144.49, 143.68, 133.88, 133.61, 132.85, 130.13 (×2), 127.71 (×2), 126.61, 120.28, 119.01, 114.31, 113.07, 113.04, 112.78, 68.72, 65.56, 59.03, 53.70, 48.02, 33.83, 28.40, 21.82, 10.05.

EXAMPLE 24

Synthesis of R(−)-N-Ethyl-2-(2-p-toluenesulfonyloxy)-propanoxynoraporphine (15d)

1.52 mmol scale; 23% isolated yield. Mp (HCl salt)=125-130° C. (decomposed). EA: $C_{27}H_{29}NO_6S \cdot HCl \cdot 1/2H_2O$: Anal. calcd. C, 60.59; H, 5.99; N, 2.52. Found: C, 60.55; H, 5.81; N, 2.45. $^1$H NMR (300 MHz, CD$_3$OD) δ 7.92 (d, J=2.5, 1H), 7.73 (d, J=8.3, 2H), 7.31 (d, J=8.0, 2H), 6.74 (q, J=8.0, 2H), 6.64 (d, J=2.5, 1H), 4.26-4.18 (m, 2H), 3.97 (t, J=5.4, 2H), 3.40-3.30 (m, 5H), 3.09 (d, J=12.8, 1H), 2.77 (t, J=13.1, 1H), 2.28 (s, 3H), 2.09 (p, J=5.9, 2H), 1.46 (t, J=7.2, 3H). $^{13}$C NMR (75 MHz, CD3OD) δ 158.44, 145.31, 145.16, 134.32, 130.70, 129.92, 128.65, 127.73, 125.71, 124.44, 120.70, 118.82, 114.85, 114.08, 111.87, 111.62, 67.24, 63.05, 60.57, 32.22, 31.64, 28.61, 26.23, 20.33, 7.92.

EXAMPLE 25

Synthesis of R(−)-2-(2-hydroxyethoxy)-10-(trifluoromethylsulfonyl)-oxy-11-hydroxyaporphine (13)

To a 10 mL Wheaton microreactor at 0° C. were added: oripavine-3-triflate (1.5 g, 3.49 mmol), anhydrous ethylene glycol (1.5 mL), and methanesulfonic acid (7.5 mL) The mixture was stirred at 0° C. for 20 minutes with occasional shaking to facilitate dissolution, then at 95° C. for 1 hour. Upon cooling, the mixture was transferred slowly to water (50 mL) The aqueous solution was basified with dropwise addition of ammonium hydroxide solution (pH 8-9). The mixture was then thoroughly extracted with dichloromethane (2×100 mL) and ethyl acetate (3×100 mL) The combined organic extracts were washed with brine, dried over sodium sulfate, filtered, and concentrated. The product crystallized out upon concentration to afford 445 mg of pale grey-green needles, 28% yield. Mp=124-126° C. $^1$H NMR (300 MHz, DMSO) δ 7.67 (s, 1H), 7.30-7.14 (m, 2H), 6.97 (t, J=9.2, 1H), 6.72 (dd, J=2.5, 12.3, 1H), 4.04-3.86 (m, 2H), 3.70 (d, J=4.3, 2H), 3.24-3.19 (m, 2H), 3.09-2.87 (m, 3H), 2.78-2.61 (m, 1H), 2.52-2.39 (m, 1H), 2.49 (s, 3H). $^{19}$F NMR (282 MHz, DMSO) δ −74.45.

EXAMPLE 26

Synthesis of R-(−)-2-hydroxyethoxy-11-hydroxyaporphine (14)

To a 6 dram vial were sequentially added: R(−)-2-hydroxyethoxy-11-hydroxy-10-[(trifluoromethane)sulfonyl] oxyaporphine (91 mg, 0.198 mmol), a magnesium turning (15 mg), 10% palladium on carbon (18 mg), and ammonium acetate (80 mg). The flask was evacuated and flushed with dry nitrogen 4 times. Next, anhydrous methanol (6 5 mL) was added, and the mixture was allowed to stir at RT with TLC monitoring. After 20 hours, the mixture was worked up by filtering through a pad of silica gel and washing with two volumes of methanol. The eluate was concentrated and directly purified by flash column chromatography (2×, using 1:10 to 1:4 methanol:dichloromethane gradient) to afford 56.2 mg of R(−)-2-hydroxyethoxy-11-hydroxyaporphine as a green glass in 91% isolated yield. $^1$H NMR (300 MHz, CD3OD) δ 7.98 (d, J=2.4, 1H), 7.02 (t, J=7.8, 1H), 6.78 (dd, J=7.8, 12.5, 2H), 6.63 (d, J=2.4, 1H), 4.02 (t, J=4.7, 2H), 3.92-3.81 (m, 2H), 3.37-3.33 (m, 1H), 3.25-3.09 (m, 3H), 2.83-2.68 (m, 2H), 2.66 (s, 3H), 2.56 (t, J=13.8, 1H). $^{13}$C NMR (75 MHz, CD3OD) δ 157.89, 154.77, 136.72, 133.57, 132.32, 128.29, 124.59, 120.46, 119.58, 115.44, 114.09, 111.83, 69.27, 62.08, 60.58, 52.75, 41.89, 34.11, 27.85.

EXAMPLE 27

Synthesis of R-(−)-2-Toluenesulfonyloxyethoxy-11-hydroxyaporphine (15g)

To a 4 dram vial under dry nitrogen were sequentially added: R-(−)-2-hydroxyethoxy-11-hydroxyaporphine (56.2 mg, 0.180 mmol), anhydrous dichloromethane (1.5 mL), and triethylamine (35 mL, 0.25 mmol). Next, a solution of tosyl chloride (34.3 mg, 0.180 mmol) in dichloromethane (0.5 mL) was added dropwise at RT. The mixture was allowed to stir overnight. After TLC analysis indicated that all the starting material had been consumed, the reaction mixture was quenched with water and washed sequentially with saturated sodium bicarbonate solution and brine (10 mL each). The organic layer was dried over sodium sulfate, filtered, and concentrated. The residue was purified by flash column chromatography using 1:15 methanol:dichloromethane as eluent to afford R-(−)-2-toluenesulfonyloxyethoxy-11-hydroxyaporphine (44 mg) which was immediately treated with ethereal hydrogen chloride to afford 50 mg of the hydrochloride salt as a pale yellow solid in 55% yield. Mp=219-221° C. (decomposes). EA: calcd ($C_{26}H_{27}NO_5S \cdot HCl \cdot H_2O$): C, 60.05; H, 5.81; N, 2.69. Found: C, 60.34; H, 5.89; N, 2.58. $^1$H NMR (300 MHz, CDCl$_3$) δ 7.28-7.22 (m, 2H), 7.16 (dd, J=3.3, 7.7, 3H), 7.09 (t, J=7.8, 1H), 6.82 (d, J=8.0, 2H), 6.49 (d, J=2.0, 1H), 3.98 (d, J=4.1, 2H), 3.92-3.82 (m, 2H), 3.10-2.99 (m, 1H), 2.98-2.87 (m, 2H), 2.62-2.31 (m, 3H), 2.39 (s, 3H), 2.30-2.22 (m, 1H), 2.20 (s, 3H). $^{13}$C NMR (75 MHz, CDCl$_3$) δ 156.86, 145.88, 144.37, 138.58, 133.73, 131.33, 130.54, 128.72, 128.30, 127.94, 127.46, 127.13, 123.17, 114.20, 112.72, 69.30, 61.39, 61.30, 52.99, 43.92, 34.83, 29.00, 21.62.

EXAMPLE 28

Synthesis of R-(−)-2-(2-fluoroethoxy)-11-hydroxyaporphine (11g)

(method A): To a 1 mL Wheaton microreactor equipped with a spin vane and open top phenolic cap with a PTFE faced silicone septum were added: Kryptofix (10.6 mg, 5 equiv), and KF (1.63 mg, 5 equiv). The vial was then evacuated and filled with nitrogen (3 cycles). Next, a solution of R(−)-2-tosyloxyethoxy-11-hydroxyaporphine (free base) (2.9 mg, 5.6 μmol; added in 500 μL of an 11.2 μM soln in anhydrous acetonitrile) was added, the vial was capped with a Mininert valve, and placed in a preheated aluminum block (80° C.) and stirred. Reaction progress was monitored by TLC and found to be complete after 20 minutes. The reaction mixture was then analyzed by HPLC analysis and confirmed to be complete and in agreement with HPLC analysis of an authentic sample.

(method B): To a 1 mL Wheaton microreactor equipped with a spin vane and open top phenolic cap with a PTFE faced silicone septum were added: Kryptofix (10.6 mg, 10 equiv), and KF (1.63 mg, 10 equiv). The vial was then evacuated and filled with nitrogen (3 cycles). Next, a solution of R-(−)-2-tosyloxyethoxy-11-hydroxyaporphine (free base) (1.5 mg, 2.8 μmol; added in 250 μL of an 11.2 μM soln in anhydrous acetonitrile) was added, the vial was capped with a Mininert valve, and placed in a preheated aluminum block (60° C.) and stirred. Reaction progress was monitored by TLC and found to be almost complete by 5 minutes, and all starting material was consumed by 13 minutes. The reaction mixture was then analyzed by HPLC analysis and confirmed to be complete and in agreement with HPLC analysis of an authentic sample.

This methodology can be used for the radiolabelling of a compound of the invention (e.g., as part of a kit used in the imaging methods of the invention).

EXAMPLE 29

In Vitro Affinity Assays

The receptor affinities of the thirteen novel compounds 6,8a-g and 11a-d, g at $D_2$ and $D_1$ dopamine receptors were assessed using competitive radioreceptor binding assays with membrane-containing homogenates of rat corpus striatum tissue, following procedures reported in detail previously (see Seeman, P. Synapse 62:314 (2008); and Si et al., J. Med. Chem. 51:983 (2008)). The results are summarized in Table 1.

TABLE 1

Affinity Affinities ($K_i$) at Dopamine $D_1$, $D_2$ and $D_3$ receptors.

| | $D_1^{low}$ [f] | $D_1^{high}$ | $D_2^{low}$ | $D_2^{high}$ | $D_3$ [g] | CLogP [d] |
|---|---|---|---|---|---|---|
| 1 | 650 ± 310 [b] | 4.6 ± 1.2 [b] | 98 ± 40 [b] | 1.8 ± 0.9 [b] | 2.6 [e] | 2.49 |
| 2a | 490 ± 220 [b] | 1 ± 0.2 [b] | 54 ± 20 [b] | 0.18 ± 0.03 [b] | 0.44 [h] | 3.55 |
| 2b [c] | Low $D_1^{low}$ | 8.1 ± 0.7 | 805 ± 140 | 5.1 ± 1.3 | 1.02 [h] | 3.51 |
| 2c | Low $D_1^{low}$ | No $D_1^{high}$ | 1800 ± 340 | 2.7 ± 1.3 | >10 μM | 3.77 |
| 3a | Low $D_1^{low}$ | No $D_1^{high}$ | 1400 ± 370 | 20 ± 6 | >10 μM | 4.10 |
| 3b | Low $D_1^{low}$ | No $D_1^{high}$ | 1410 ± 220 | 4.9 ± 1.2 | 1700 ± 250 | 4.15 |
| 6 | Low $D_1^{low}$ | No $D_1^{high}$ | 860 ± 170 | 6.9 ± 2.1 | >10 μM | 3.57 |
| 8a | Low $D_1^{low}$ | No $D_1^{high}$ | 3000 | 28 ± 15 | 430 ± 64 | 3.99 |
| 8b | Low $D_1^{low}$ | No $D_1^{high}$ | 990 ± 35 | 3.7 ± 1.2 | 2200 ± 330 | 3.77 |
| 11a | Low $D_1^{low}$ | No $D_1^{high}$ | 490 ± 280 | 0.54 ± 1.6 | 100 ± 14 [i] | 4.58 |
| 11b | Low $D_1^{low}$ | No $D_1^{high}$ | 56 ± 37 | 3.5 ± 2.0 | 410 ± 62 [i] | 4.35 |
| 8c | Low $D_1^{low}$ | No $D_1^{high}$ | 1600 ± 780 | 6.1 ± 3 | >10 μM | 3.47 |
| 8d | Low $D_1^{low}$ | No $D_1^{high}$ | 2400 ± 1500 | 2.5 ± 0.8 | >10 μM | 3.24 |
| 8e | Low $D_1^{low}$ | No $D_1^{high}$ | 770 ± 230 | 5 ± 2.3 | >10 μM | NA |
| 11c | 1300 ± 200 [j] | No $D_1^{high}$ | 400 ± 290 | 3.2 ± 2.2 | 240 ± 33 [i] | 4.05 |
| 11d | 810 ± 120 [j] | No $D_1^{high}$ | 750 ± 560 | 0.83 ± 0.60 | 550 ± 89 [i] | 3.82 |
| 8f | Low $D_1^{low}$ | No $D_1^{high}$ | >10 μM | 31 ± 9 | >10 μM | 2.94 |
| 8g | Low $D_1^{low}$ | No $D_1^{high}$ | 620 ± 260 | 2.0 ± 096 | >10 μM | 2.71 |
| 11g | 340 ± 44 | No $D_1^{high}$ | 480 ± 130 | 1.2 ± 0.4 | 890 ± 130 | 3.29 |

[a] Radioligands: $D_1$: rat striatum [$^3$H]SCH23390; $D_2$: rat striatum [$^3$H] domperidone. $D_3$: human $D_3$ clone [$^3$H]domperidone; errors are expressed as standard deviations.
[b] Data from Seeman, P. Synapse 61:1013 (2007).
[c] For preparation see Gao et al., J. Med. Chem. 33: 1800 (1990).
[d] Calculated using the chemical properties feature in CambridgeSoft ChemDraw Ultra, version 12.0.
[e] Data from Seeman, et al., Synapse 58: 122 (2005).
[f] Low $D_1^{low}$ = >2 μM.
[g] The following compounds were also found to have $D_3^{high}$ affinity: 2c (3.8 ± 2 nM), 3a (130 ± 100 nM), 3b (1.2 ± 1 nM), 8a (1.1 ± 2 nM), 8b (1.9 ± 1.5 nM), 8c (230 ± 140 nM), and 8d (250 ± 19 nM).
[h] See Skinberg et al., Synapse 63: 462 (2009); HEK293T cell homogenate used with [$^3$H]methylspiperone.
[i] Source and radioligands: $D_3$ rat clone [$^3$H] domperidone.
[j] Source and radioligands: $D_1$ human clone [$^3$H]SCH23390.

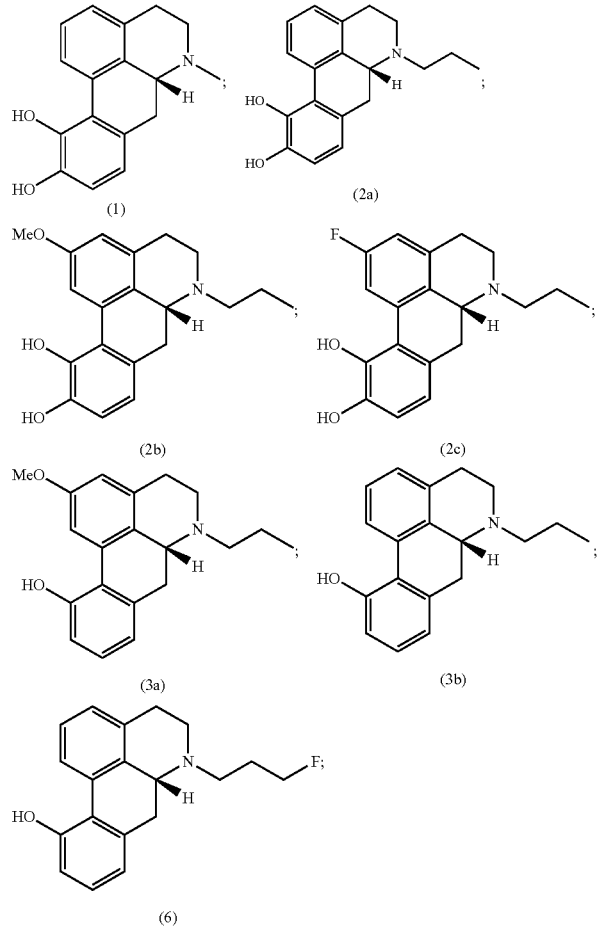

TABLE 1-continued

Affinity Affinities (K$_i$) at Dopamine D$_1$, D$_2$ and D$_3$ receptors.

K$_i$ (nM) $^a$

| D$_1$$^{low\,f}$ | D$_1$$^{high}$ | D$_2$$^{low}$ | D$_2$$^{high}$ | D$_3$$^g$ | CLogP $^d$ |
| --- | --- | --- | --- | --- | --- |

TABLE 1-continued

Affinity Affinities ($K_i$) at Dopamine $D_1$, $D_2$ and $D_3$ receptors.

| $D_1^{low\,f}$ | $D_1^{high}$ | $D_2^{low}$ | $D_2^{high}$ | $D_3{}^g$ | CLogP $^d$ |
|---|---|---|---|---|---|

(11c)

(11d)

(8f)   (8g)

(11g)

Other Embodiments

All publications, patents, and patent applications mentioned in this specification are incorporated herein by reference to the same extent as if each independent publication or patent application was specifically and individually indicated to be incorporated by reference. This application claims benefit of the U.S. Provisional Application No. 61/324,081, filed Apr. 14, 2010, and is incorporated herein by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound of formula I:

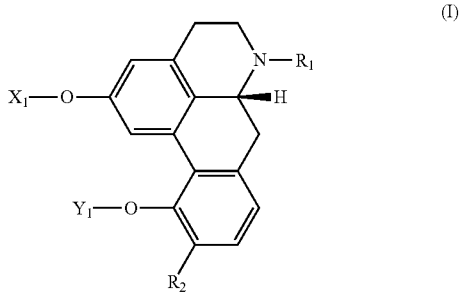

(I)

or a pharmaceutically acceptable salt thereof,
wherein
$X_1$ is 2-fluoroethyl, 3-fluoro-n-propyl, 2-iodoethyl, or 3-iodo-n-propyl;
$R_1$ is H, $CH_3$, $CH_2CH_3$, or $CH_2CH_2CH_3$;
$R_2$ is H or $OY_2$;

each of $Y_1$ and $Y_2$ is, independently, selected from H, C(O)—$R_3$, and fatty acid acyl, and $R_3$ is selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, wherein said compound has an in vitro affinity of between 0.5 nM and 35 nM at $D_2^{high}$ receptors.

2. The compound of claim 1, wherein $X_1$ is a 2-fluoroethyl or 3-fluoro-n-propyl substituent, and wherein said 2-fluoroethyl or 3-fluoro-n-propyl substituent comprises a radioactive fluorine atom.

3. The compound of claim 1, wherein said compound is selected from R(−)-2-(2-fluoroethoxy)-11-hydroxy-N-methyl-noraporphine, R(−)-2-(3-fluoro-n-propanoxy)-11-hydroxy-N-methyl-noraporphine, R(−)-2-(2-fluoroethoxy)-11-hydroxy-N-ethyl-noraporphine, R(−)-2-(3-fluoro-n-propanoxy)-11-hydroxy-N-ethyl-noraporphine, R(−)-2-(2-fluoroethoxy)-11-hydroxy-N-propyl-noraporphine, R(−)-2-(3-fluoro-n-propanoxy)-11-hydroxy-N-propyl-noraporphine, esters thereof, and pharmaceutically acceptable salts thereof.

4. The compound of claim 1, wherein said compound is selected from R(−)-2-(2-fluoroethoxy)-10-hydroxy-11-hydroxy-N-methyl-noraporphine, R(−)-2-(3-fluoro-n-propanoxy)-10-hydroxy-11-hydroxy-N-methyl-noraporphine, R(−)-2-(2-fluoroethoxy)-10-hydroxy-11-hydroxy-N-ethyl-noraporphine, R(−)-2-(3-fluoro-n-propanoxy)-10-hydroxy-11-hydroxy-N-ethyl-noraporphine, R(−)-2-(2-fluoroethoxy)-10-hydroxy-11-hydroxy-N-propyl-noraporphine, R(−)-2-(3-fluoro-n-propanoxy)-10-hydroxy-11-hydroxy-N-propyl-noraporphine, monoesters thereof, diesters thereof, and pharmaceutically acceptable salts thereof.

5. The compound of claim 1, wherein said compound has no observable affinity at $D_1^{high}$ receptors.

6. A method of imaging $D_2^{high}$ receptors in a subject, said method comprising (i) administering to said subject a radiolabeled compound of claim 1, and (ii) following the specific binding of said radiolabeled compound to said $D_2^{high}$ receptors, monitoring the distribution of said radiolabeled compound in said subject.

7. The method of claim 6, wherein said radiolabeled compound comprises a radioactive fluorine atom.

8. The method of claim 7, wherein said distribution of said radiolabeled compound in said subject is monitored using PET.

9. The method of claim 6, wherein said radiolabeled compound comprises a radioactive iodine atom.

10. The method of claim 9, wherein said distribution of said radiolabeled compound in said subject is monitored using SPECT.

11. The method of claim 6, further comprising diagnosing a dopamine-related disorder in said subject on the basis of the results of said imaging.

12. The method of claim 6, wherein in said imaging is repeated to monitor the progression of a dopamine-related disorder in said subject.

13. The method of claim 11, wherein said dopamine-related disorder is selected from psychoses, schizophrenia, Parkinson's disease, and progressive supranuclear palsy.

14. The method of claim 11, wherein said dopamine-related disorder is dopamine supersensitivity.

15. A method of treating Parkinson's disease in a subject, said method comprising administering to said subject an effective amount of a compound of claim 1.

16. The compound of claim 1, wherein $X_1$ is 2-fluoroethyl, $R_1$ is $CH_2CH_2CH_3$, $R_2$ is H, and $Y_1$ is H, or a pharmaceutically acceptable salt thereof.

17. The compound of claim 1, wherein $X_1$ is 2-fluoroethyl, $R_1$ is $CH_2CH_2CH_3$, $R_2$ is OH, and $Y_1$ is H, or a pharmaceutically acceptable salt thereof.

18. The compound of claim 1, wherein $X_1$ is 3-fluoro-n-propyl, $R_1$ is $CH_2CH_2CH_3$, $R_2$ is H, and $Y_1$ is H, or a pharmaceutically acceptable salt thereof.

* * * * *

UNITED STATES PATENT AND TRADEMARK OFFICE
CERTIFICATE OF CORRECTION

PATENT NO. : 9,517,279 B2
APPLICATION NO. : 13/640426
DATED : December 13, 2016
INVENTOR(S) : John L. Neumeyer et al.

It is certified that error appears in the above-identified patent and that said Letters Patent is hereby corrected as shown below:

In the Specification

Column 2, Line 31, replace "interacts with the G, complex" with --interacts with the $G_s$ complex--;
    Lines 32-33, replace "interacts with G, to inhibit" with --interacts with $G_i$ to inhibit--.

Column 9, Lines 25-26, replace "intraparenchemal" with --intraparenchymal--.

Column 12, Line 18, replace "saturated partially unsaturated or unsaturated" with
        --saturated, partially unsaturated, or unsaturated--.

Column 17, Line 52, replace "according the published procedure" with
        --according to the published procedure--.

Column 21, Lines 9-10, replace "hydrogenated napthalenes" with --hydrogenated naphthalenes--;
    Lines 28-29, replace "such as a non-toxic acid addition salts" with
        --such as non-toxic acid addition salts--.

Column 22, Line 60, replace "nigrostrial" with --nigrostriatal--.

Column 23, Line 30, replace "8 value (ppm)" with --δ value (ppm)--.

Column 24, Line 32, replace "$C_{19}C_{20}NOF.HCl.0.5H_2O$" with --$C_{19}C_{20}NOF•HCl•0.5H_2O$--;
    Line 47, replace "[(trifluoromethyesulfonyl]" with --[(trifuloromethyl)sulfonyl]--;
    Line 59, replace "(2×50 mL) The" with --(2×50 mL). The--.

Column 28, Line 16, replace "(6 mL) The resulting" with --(6 mL). The resulting--;
    Line 19, replace "(0 5 mL)" with --(0.5 mL)--;
    Line 65, replace "MeOH (5.0 mL) The" with --MeOH (5.0 mL). The--.

Signed and Sealed this
Twentieth Day of February, 2018

Andrei Iancu
*Director of the United States Patent and Trademark Office*

Column 29, Line 9, replace "$C_{20}H_{23}NO.HCl.0.5H_2O$" with --$C_{20}H_{23}NO \cdot HCl \cdot 0.5H_2O$--;
   Line 56, replace "mL) The residue" with --mL). The residue--;
   Line 64, replace "$C_{21}H_{24}FNO_2.0.38CH_3OH.0.063CH_2Cl_2$" with
        --$C_{21}H_{24}FNO_2 \cdot 0.38CH_3OH \cdot 0.063CH_2Cl_2$--.

Column 30, Line 66, replace "$C_{20}H_{22}FNO_2$ xHClx0.6H_2O" with --$C_{20}H_{22}FNO_2 \cdot HCl \cdot 0.6H_2O$--.

Column 31, Line 59, replace "alcohol (0 5 mL)" with --alcohol (0.5 mL)--.

Column 32, Line 25, replace "$C_{22}H_{26}NFO_3.HCl$" with --$C_{22}H_{26}NFO_3 \cdot HCl$--;
   Line 58, replace "$C_{21}H_{24}NFO_3.HCl.1.25H_2O$" with --$C_{21}H_{24}NFO_3 \cdot HCl \cdot 1.25H_2O$--.

Column 33, Line 22, replace "$C_{21}H_{24}NFO_3.HCl.H_2O$" with --$C_{21}H_{24}NFO_3 \cdot HCl \cdot H_2O$--;
   Line 56, replace "$C_{20}H_{22}NFO_3.HCl.0.75H_2O$" with --$C_{22}H_{22}NFO_3 \cdot HCl \cdot 0.75H_2O$--.

Column 34, Line 23, replace "$C_{20}H_{22}FNO_3.HCl.1/3H_2O$" with --$C_{20}H_{22}FNO_3 \cdot HCl \cdot 1/3H_2O$--;
   Line 57, replace "$C_{19}H_{20}FNO_3.HCl$" with --$C_{19}H_{20}FNO_3 \cdot HCl$--.

Column 35, Line 50, replace "$C_{20}H_{22}INO_3.HCl.3/4H_2O$" with --$C_{20}H_{22}INO_3 \cdot HCl \cdot 3/4H_2O$--.

Column 36, Line 29, replace "$C_{26}H_{27}NO_6S.HCl.1/3H_2O$" with --$C_{26}H_{27}NO_6S \cdot HCl \cdot 1/3H_2O$--;
   Line 48, replace "$C_{27}H_{29}NO_6S.HCl.1/2H_2O$" with --$C_{27}H_{29}NO_6S \cdot HCl \cdot 1/2H_2O$--.

Column 37, Line 1, replace "(7.5 mL) The" with --(7.5 mL). The--;
   Line 5, replace "(50 mL) The aqueous" with --(50 mL). The aqueous--;
   Line 8, replace "ethyl acetate (3×100 mL) The" with --"ethyl acetate (3×100 mL). The--;
   Line 29, replace "methanol (6 5 mL)" with --methanol (6.5 mL)--.

Column 38, Line 2, replace "($C_{26}H_{27}NO_5S.HCl.H_2O$)" with --($C_{26}H_{27}NO_5S \cdot HCl \cdot H_2O$)--.